US010532061B2

(12) United States Patent
Pellicciari

(10) Patent No.: US 10,532,061 B2
(45) Date of Patent: *Jan. 14, 2020

(54) FARNESOID X RECEPTOR MODULATORS

(71) Applicant: Intercept Pharmaceuticals, Inc., New York, NY (US)

(72) Inventor: Roberto Pellicciari, Perugia (IT)

(73) Assignee: Intercept Pharmaceuticals, Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/124,139

(22) Filed: Sep. 6, 2018

(65) Prior Publication Data

US 2019/0209586 A1 Jul. 11, 2019

Related U.S. Application Data

(63) Continuation of application No. 15/434,685, filed on Feb. 16, 2017, now abandoned, which is a continuation of application No. 14/120,366, filed on May 14, 2014, now Pat. No. 9,611,289.

(60) Provisional application No. 61/823,169, filed on May 14, 2013.

(30) Foreign Application Priority Data

May 14, 2014 (EP) .................. PCT/EP2014/059896

(51) Int. Cl.
A61K 31/575 (2006.01)
C07J 9/00 (2006.01)
A61P 1/16 (2006.01)
A61P 1/00 (2006.01)
C07J 41/00 (2006.01)
C07J 31/00 (2006.01)
C07J 71/00 (2006.01)

(52) U.S. Cl.
CPC .............. A61K 31/575 (2013.01); A61P 1/00 (2018.01); A61P 1/16 (2018.01); C07J 9/005 (2013.01); C07J 41/0061 (2013.01); C07J 31/006 (2013.01); C07J 71/001 (2013.01)

(58) Field of Classification Search
CPC .. A61K 31/575; A61P 1/00; A61P 1/16; C07J 9/005
See application file for complete search history.

(56) References Cited

U.S. PATENT DOCUMENTS 2,802,775 A 8/1957 Dulaney et al.
9,611,289 B2 4/2017 Pellicciari et al.
2017/0216316 A1 8/2017 Pellicciari et al.

FOREIGN PATENT DOCUMENTS

EP 0124903 B1 3/1987
EP 1568706 A1 8/2005
WO WO 2000/037077 A1 6/2000
WO WO 2004/007521 A2 1/2004

OTHER PUBLICATIONS

Bidstrup, T.B., et al. "CYP2C8 and CYP3A4 are the principal enzymes involved in the human in vitro biotransformation of the insulin secretagogue repaglinide," Br. J Clin Pharmacol. 56(3):305-314 (2003).
Cree, I.A., et al. "Measurement of cytotoxicity by ATP-based luminescence assay in primary cell cultures and cell lines," Toxicology in Vitro, 11(5):553-556 (1997).
Crouch, S.P.M., et al. "The use of ATP bioluminescence as a measure of cell proliferation and cytotoxicity," Journal of Immunol. Methods, 160(1):81-88 (1993).
De Marino, S., et al. "Theonellasterols and conicasterols from Theonella swinhoei. Novel marine natural ligands for human nuclear receptors," J. Med. Chem., 54(8):3065-3075 (2011).
Ding, et al., "Bile acid nuclear receptor FXR and digestive system diseases," Acta Pharmaceutica Sinica B, vol. 5, No. 2, pp. 135-144 (2015).
Dorn, A., et al. "Evaluation of a high-throughput fluorescence assay method for hERG potassium channel inhibition," J. Biomol. Screening, 10(4):339-347 (2005).
Forman, B.M., et al. "Identification of a nuclear receptor that is activated by farnesol metabolites," Cell, 81:687-693 (1995).
Goodwin, B., et al. "A regulatory cascade of the nuclear receptors FXR, SHP-1, and LRH-1 represses bile acid biosynthesis," Mol. Cell, 6(3):517-526 (2000).
Heery, D.M., et al. "A signature motif in transcriptional co-activators mediates binding to nuclear receptors," Nature, 387:733-736 (1997).
Huber, R.M., et al. "Generation of multiple farnesoid-X-receptor isoforms through the use of alternative promoters," Gene, 290(1-2):35-43 (2002).

(Continued)

Primary Examiner — Barbara P Badio
(74) Attorney, Agent, or Firm — Michelle Iwamoto-Fan; Intercept Pharmaceuticals, Inc.

(57) ABSTRACT

The present invention provides a compound of formula (I):

or a pharmaceutically acceptable salt, solvate, or amino acid conjugate thereof, wherein $R^1$, $R^2$, $R^3$, $R^4$, $R^5$, and $R^6$ are as described herein. The present invention relates generally to selective FXR agonists and to methods of making and using them.

6 Claims, 9 Drawing Sheets

(56) References Cited

OTHER PUBLICATIONS

Ishida, H., et al. "Study on the bile salts from Sunfish, *Mola mola* L. I. The Structures of Sodium Cyprinol Sulfates, the Sodium Salt of a New Bile Acid Conjugated with Taurine, and a New Bile Alcohol and Its New Sodium Sulfates," Chem. Pharm. Bull., 46(1):12-16 (1998).
Kangas, L., et al. "Bioluminescence of cellular ATP: a new method for evaluating cytotoxic agents in vitro," Medical Biology, 62(6):338-343 (1984).
Kast, H.R., et al. "Farnesoid X-activated receptor induces apolipoprotein C-11 transcription: a molecular mechanism linking plasma triglyceride levels to bile acids," Mol. Endocrinol., 15(10):1720-1728 (2001).
Kawamata, Y., et al. "A G protein-coupled receptor responsive to bile acids," J. Biol. Chem., 278(11):9435-9440 (2003).
Lambert, G., et al. "The farnesoid X-receptor is an essential regulator of cholesterol homeostasis," J. Biol. Chem., 278(4), 2563-70 (2003).
Long, W.P., et al. "Partial synthesis of compounds related to adrenal cortical hormones: III. Preparation of 3(a),11(a)-dihydroxycholanic acid," J. Biol. Chem., 162(3):511-519 (1946).
Ma, K., et al. "Farnesoid X receptor is essential for normal glucose homeostasis," J. Clin. Invest., 116(4):1102-1109 (2006).
Makishima, M., et al. "Identification of a nuclear receptor for bile acids," Science, 284:1362-1365 (1999).
Mangelsdorf, D.J., et al. "The RXR heterodimers and orphan receptors," Cell, 83(6):841-850 (1995).
Maruyama, T., et al. "Identification of membrane-type receptor for bile acids (M-BAR)," Biochem. Biophys. Res. Commun., 298(5):714-719 (2002).
Massafra, et al. "Splenic dendritic cell involvement in FXR-mediated amelioration of DSS colitis", Biochimica et Biophysica Acta vol. 1862, pp. 166-173 (2016).
Nijmeijer et al., "Farnesoid X receptor (FXR) activation and FXR genetic variation in inflammatory bowel disease" PLoS ONE, vol. 6(8), pp. 1-6, (2011).
Nolte, R.T., et al. "Ligand binding and co-activator assembly of the peroxisome proliferator-activated receptor-gamma," Nature, 395:137-143 (1998).
Obach, R.S., et al. "The utility of in vitro cytochrome P450 inhibition data in the prediction of drug-drug interactions," J. Pharmcol. Exp. Ther., 316(1):336-48 (2006).
Onate, S.A., et al. "Sequence and characterization of a coactivator for the steroid hormone receptor superfamily," Science, 270: 1354-1357 (1995).
Parks, D.J., et al. "Bile acids: natural ligands for an orphan nuclear receptor," Science, 284:1365-1368 (1999).
Pellicciari, R., et al. "6a-ethyl-chenodeoxycholic acid (6-ECDCA), a potent and selective FXR agonist endowed with anticholestatic activity," J. Med. Chem., 45(17): 3569-72 (2002).
Pellicciari, R., et al. "Bile acid derivatives as ligands of the farnesoid X receptor. Synthesis, evaluation, and structure-activity relationship of a series of body and side chain modified analogues of chenodeoxycholic acid", J. Med. Chem., 47(18):4559-4569 (2004).
Petty, R.D., et al. Comparison of MTT and ATP-based assays for the measurement of viable cell number, J. Biolumin Chemilumin 10(1): 29-34 (1995).
Rizzo, G., et al. "Functional characterization of the semisynthetic bile acid derivative INT-767, a dual farnesoid X receptor and TGR5 agonist," Mol. Pharm., 78(4): 617-630 (2010).
Russell, D.W. "Nuclear Orphan Receptors Control Cholesterol Catabolism," Cell, 97(5):539-542 (1999).
Schinkel, A.H., et al. "Mammalian drug efflux transporters of the ATP binding cassette (ABC) family: an overview," Adv. Drug Deliv. Rev., 64:138-153 (2012).
Seol, W. et al. "Isolation of proteins that interact specifically with the retinoid X receptor: two novel orphan receptors," Mol. Endocrinol., 9(1):72-85 (1995).
Stojancevic Mpharm, Maja et al. "The impact of farnesoid X receptor activation on intestinal permeability in inflammatory bowel disease", Can J Gastroenterol, vol. 26, No. 9, p. 631-637 (2012).
Storer, R.D., et al. "Revalidation of the in vitro alkaline elution/rat hepatocyte assay for DNA damage: improved criteria for assessment of cytotoxicity and genotoxicity and results for 81 compounds," Mutat. Res., 368(2): 59-101 (1996).
Sussman, N.L., "The Predictive Nature of High-Throughput Toxicity Screening Using a Human Hepatocyte Cell Line," Promega Cell Notes, 3:7-10 (2002).
Torchia, J., et al. "The transcriptional co-activator p/CIP binds CBP and mediates nuclear-receptor function," Nature, 387:677-684 (1997).
Walters, et al. "The response of patients with bile acid diarrhoea to the farnesoid X receptor agonist obeticholic acid", Aliment Pharmacol Ther vol. 41, pp. 54-64 (2015).
Wang, J.C., et. al. "SRC-1 and GRIP1 coactivate transcription with hepatocyte nuclear factor 4," J. Biol. Chem., 273(47):30847-30850 (1998).
Watanabe, M. et al. "Bile acids lower triglyceride levels via a pathway involving FXR, SHP, and SREBP-1c," J. Clin. Invest., 113(10):1408-1418 (2004).
Zhang, J.H. et al. "A Simple Statistical Parameter for Use in Evaluation and Validation of High Throughput Screening Assays," J. Biomol. Screening, 4(2):67-73 (1999).
Zhang, et al., "Potent stimulation of fibroblast growth factor 19 expression in the human ileum by bile acids", Am J Physiol Gastrointest Liver Physiol vol. 304, pp. G940-G948 (2013).
Zhu, Y, et al. "Cloning and identification of mouse steroid receptor coactivator-1 (mSRC-1), as a coactivator of peroxisome proliferator-activated receptor-gamma," Gene Expr, 6(3):185-195 (1996).

Figure 4
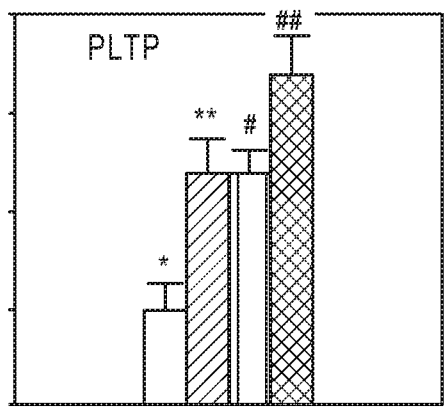
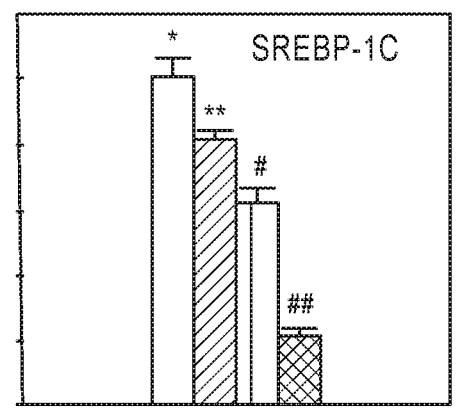
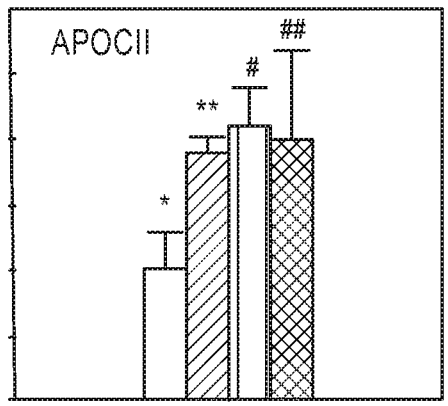
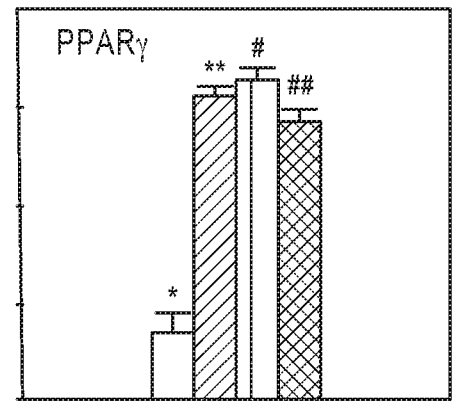
\* ☐ NT
\*\* ▨ INT-747 1μM
\# ☐ INT-767 1μM
\#\# ▩ Cmpd 100 1μM

C

FARNESOID X RECEPTOR MODULATORS

BACKGROUND OF THE INVENTION

FXR is a member of the nuclear receptor family of ligand-activated transcription factors that includes receptors for the steroid, retinoid, and thyroid hormones (D. J. Mangelsdorf, et al., Cell 83:841-850 (1995)). Northern and in situ analysis show that FXR is most abundantly expressed in the liver, intestine, kidney, and adrenal (B. M. Forman, et al., Cell 81:687-693 (1995) and W. Seol, et al., Mol. Endocrinol. 9:72-85 (1995)). FXR binds to DNA as a heterodimer with the 9-cis retinoic acid receptor (RXR). The rat FXR is activated by micromolar concentrations of farnesoids such as farnesol and juvenile hormone (B. M. Forman, et al., Cell 81:687-693 (1995)). However, these compounds failed to activate the mouse and human FXR, leaving the nature of the endogenous FXR ligands in doubt. Several naturally-occurring bile acids (e.g., chenodeoxycholic acid (CDCA), deoxycholic acid (DCA), lithocholic acid (LCA), and the taurine and glycine conjugates thereof) serve as FXR ligands and bind to and activate FXR at physiological concentrations (WO 00/37077).

Bile acids are cholesterol metabolites that are formed in the liver and secreted into the duodenum of the intestine, where they have important roles in the solubilization and absorption of dietary lipids and vitamins. Most bile acids (~95%) are subsequently reabsorbed in the ileum and returned to the liver via the enterohepatic circulatory system. The conversion of cholesterol to bile acids in the liver is under feedback regulation: bile acids down-regulate the transcription of cytochrome P450 7a (CYP7a), which encodes the enzyme that catalyzes the rate limiting step in bile acid biosynthesis. It is suggested that FXR is involved in the repression of CYP7a expression by bile acids (D. W. Russell, Cell 97:539-542 (1999)). In the ileum, bile acids induce the expression of the intestinal bile acid binding protein (IBABP), which binds bile acids with high affinity and may be involved in their cellular uptake and trafficking. It is demonstrated that bile acids mediate their effects on IBABP expression through activation of FXR, which binds to an IR-1 type response element that is conserved in the human, rat, and mouse IBABP gene promoters. Thus, FXR is involved in both the stimulation (IBABP) and the repression (CYP7a) of target genes involved in bile acid and cholesterol homeostasis. Accordingly, there is a need for FXR modulators suitable for drug development. The present invention addresses this need.

SUMMARY OF THE INVENTION

The invention provides compounds and methods of preparing these compounds. Specifically, the invention provides a compound of formula I:

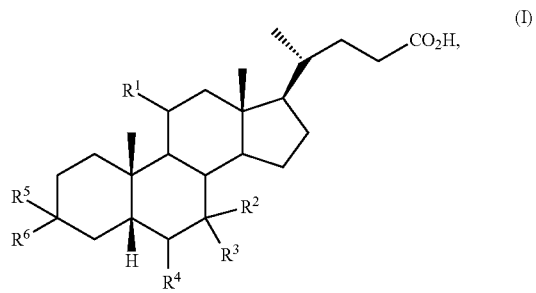

or a pharmaceutically acceptable salt, solvate, or amino acid conjugate thereof, wherein $R^1$, $R^2$, $R^3$, $R^4$, $R^5$ and $R^6$ are as described herein. The compounds of the invention are useful for treating and preventing diseases and conditions.

The invention also provides a pharmaceutical composition comprising a compound of the invention or a pharmaceutically acceptable salt, solvate, or amino acid conjugate thereof, and a pharmaceutically acceptable carrier or excipient.

The invention also provides a method for the treatment or prevention of a disease and condition, comprising administering to the subject in need thereof an effective amount of a compound of the invention or a pharmaceutically acceptable salt, solvate, or amino acid conjugate thereof. In one aspect, the disease or condition is FXR-mediated.

The invention also provides for the manufacture of a medicament for treating or preventing a disease or condition (e.g., a disease or condition mediated by FXR), wherein the medicament comprises a compound of the invention or a pharmaceutically acceptable salt, solvate, or amino acid conjugate thereof.

The invention also provides a composition for use in a method for treating or preventing a disease or condition (e.g., a disease or condition mediated by FXR), wherein the composition comprises a compound of the invention or a pharmaceutically acceptable salt, solvate, or amino acid conjugate thereof.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIG. 4 is a series of graphs showing the activity of a compound of the invention and other comparison compounds in regulating PLTP involved in lipid metabolism (A), SREBP-IC (B), APOCII (C), and PPARγ (D).

DETAILED DESCRIPTION OF THE INVENTION

Compounds of the Invention

Figure 1:
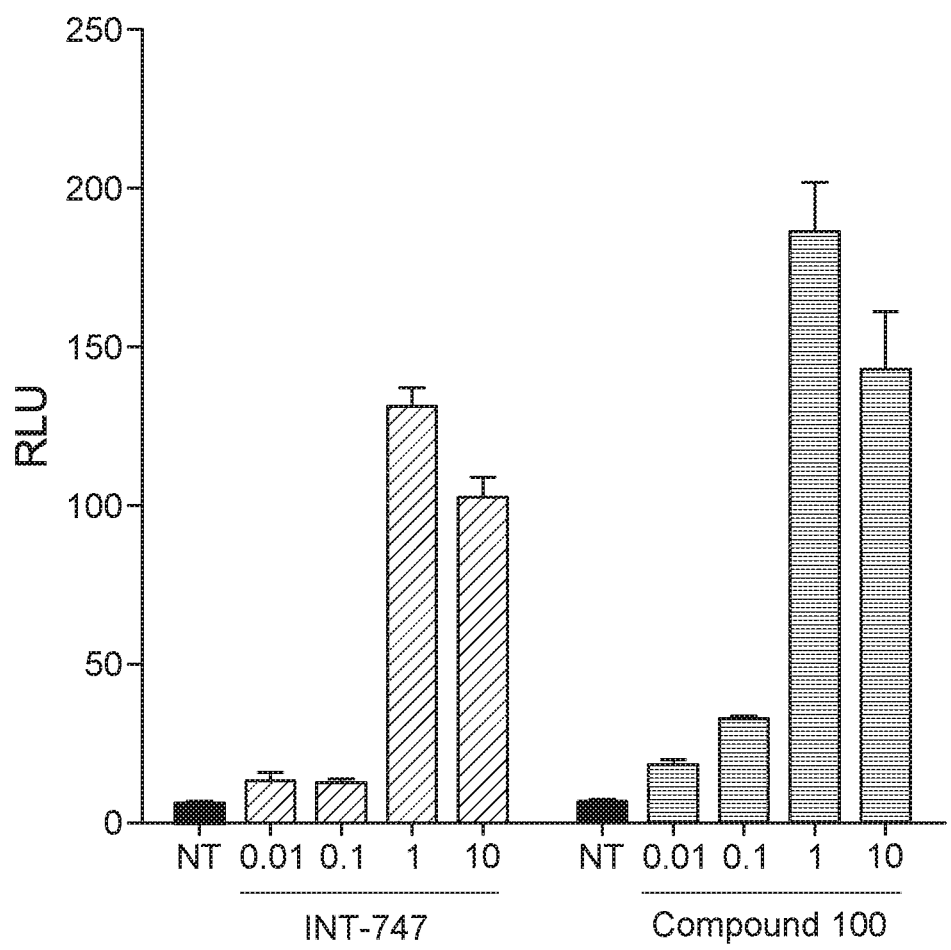
FIG. 1 is a graph showing the activity of a compound of the invention and a comparison compound in a transactivation assay in HEK293T cells

The present invention relates to a compound of formula I:

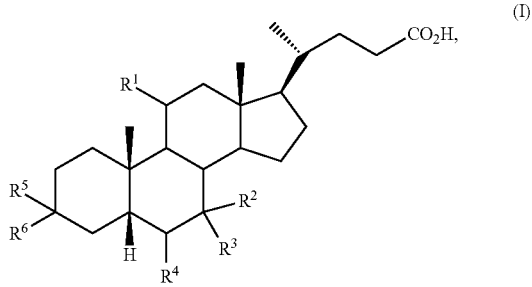

(I)

or a pharmaceutically acceptable salt, solvate, or amino acid conjugate thereof, wherein:

$R^1$ is hydroxyl;

$R^2$ is hydrogen, hydroxyl, alkyl, or halogen, wherein said alkyl is unsubstituted or substituted with one or more $R^a$;

$R^3$ is hydrogen, hydroxyl, alkyl, or halogen, wherein said alkyl is unsubstituted or substituted with one or more $R^b$;

$R^4$ is hydrogen, alkyl, alkenyl, alkynyl, or halogen, wherein said alkyl is unsubstituted or substituted with one or more $R^c$;

$R^a$, $R^b$, and $R^c$ are each independently halogen or hydroxyl;

$R^5$ is hydroxyl, $OSO_3H$, $OSO_3^-$, $OCOCH_3$, $OPO_3H$, $OPO_3^{2-}$, or hydrogen; and $R^6$ is hydroxyl, $OSO_3H$, $OSO_3^-$, $OCOCH_3$, $OPO_3H$, $OPO_3^{2-}$, or hydrogen;

or taken together $R^5$ and $R^6$ with the carbon atom to which they are attached form a carbonyl.

In one aspect, the present invention relates to a compound formula II:

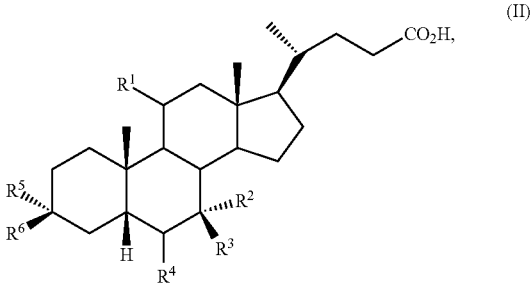

(II)

or a pharmaceutically acceptable salt, solvate, or amino acid conjugate thereof.

In one aspect, the present invention relates to a compound of formula III:

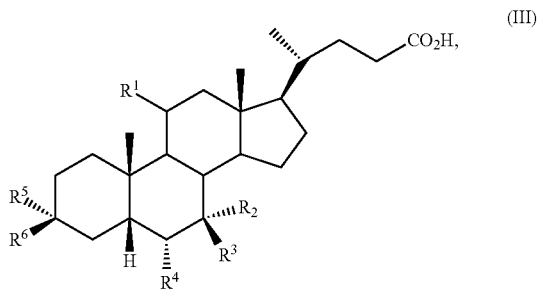

(III)

or a pharmaceutically acceptable salt, solvate, or amino acid conjugate thereof.

In one aspect, the present invention relates to a compound of formula IV:

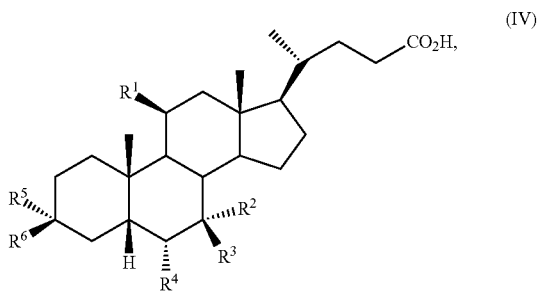

(IV)

or a pharmaceutically acceptable salt, solvate, or amino acid conjugate thereof.

In one aspect, the present invention relates to a compound of formula I, II, III, or IV, wherein the compound is the compound (e.g., the native compound, or the compound in the non-salt, unsolvateed, and non-conjuated form).

In one aspect, the present invention relates to a compound of formula I, II, III, or IV, wherein the compound is the pharmaceutically acceptable salt.

In one aspect, the present invention relates to a compound of formula I, II, III, or IV, wherein the compound is the amino acid conjugate. In one aspect, the amino acid conjugate is a glycine conjugate. In one aspect, the amino acid conjugate is a taurine conjugate.

In one aspect, the present invention relates to a compound of formula I, wherein one of $R^2$ or $R^3$ is hydroxyl or halogen and the remaining $R^2$ or $R^3$ is hydrogen or unsubstituted alkyl. In one aspect, one of $R^2$ or $R^3$ is hydroxyl and the remaining $R^2$ or $R^3$ is hydrogen.

In one aspect, the present invention relates to a compound of formula I, wherein one of $R^5$ or $R^6$ is hydroxyl and the remaining $R^5$ or $R^6$ is hydrogen.

In one aspect, the present invention relates to a compound of formula I, II, III, or IV, wherein $R^2$ is hydroxyl or halogen. In one aspect, $R^2$ is hydroxyl. In another aspect, $R^2$ is halogen.

In one aspect, the present invention relates to a compound of formula I, II, III, or IV, wherein $R^3$ is hydrogen or unsubstituted alkyl. In one aspect, $R^3$ is hydrogen. In another aspect, $R^3$ is methyl.

In one aspect, the present invention relates to a compound of formula I, II, III, or IV, wherein $R^2$ is hydroxyl and $R^3$ is hydrogen.

In one aspect, the present invention relates to a compound of formula I, II, III, or IV, wherein $R^5$ is hydroxyl.

In one aspect, the present invention relates to a compound of formula I, II, III, or IV, wherein $R^6$ is hydrogen.

In one aspect, the present invention relates to a compound of formula I, II, III, or IV, wherein $R^2$ and $R^5$ are each hydroxyl and $R^3$ and $R^6$ are each hydrogen.

In one aspect, the present invention relates to a compound of formula I, II, III, or IV, wherein $R^4$ is alkyl or hydrogen. In one aspect, the present invention relates to a compound of formula I, II, III, or IV, wherein $R^4$ is unsubstituted alkyl. In one aspect, $R^4$ is methyl, ethyl, propyl, or butyl. In one aspect, $R^4$ is methyl or ethyl. In one aspect, $R^4$ is methyl. In one aspect, $R^4$ is ethyl.

In one aspect, the present invention relates to compound

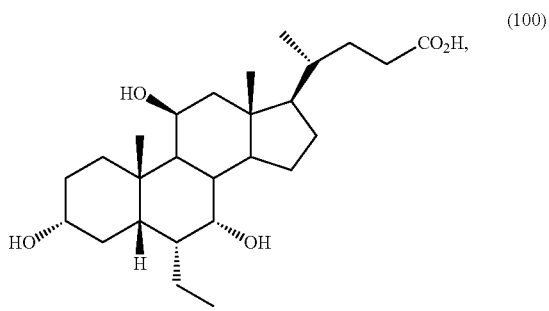 [SMILES: CC[C@H]1[C@@H](O)C2C3CC[C@H]([C@H](C)CCC(=O)O)[C@@]3(C)C[C@H](O)C2[C@@]2(C)CC[C@@H](O)C[C@@H]12]

(100)

or a pharmaceutically acceptable salt, solvate, or amino acid conjugate thereof.

In one aspect, the present invention relates to a compound of formula I, II, III, or IV, wherein the compound is an FXR agonist. In one aspect, the compound of the invention is a highly potent FXR agonist. For example, the compound of the invention activates FXR at a concentration below 1 μM, below 0.8 μM, below 0.6 μM, below 0.4 μM, or below 0.2 μM (e.g., as measured by an AlphaScreen assay), as compared to 15 μM for CDCA. For example, the compound of the invention activates FXR at a concentration below 0.2 μM (e.g., as measured by an AlphaScreen assay). For example, the compound of the invention activates FXR with an $EC_{50}$ below 1 μM, below 0.8 μM, below 0.6 μM, below 0.4 μM, or below 0.2 μM (e.g., as measured by an AlphaScreen assay), as compared to 8.9 μM for CDCA. For example, the compound of the invention activates FXR with an $EC_{50}$ below 0.2 μM (e.g., as measured by an AlphaScreen assay).

In one aspect, the present invention relates to a compound of formula I, II, III, or IV, wherein the compound is not active against other nuclear receptors. In one aspect, the present invention relates to a compound of formula I, II, III, or IV, wherein the compound does not activate TGR5 (e.g., as measured by an HTR-FRET TGR5 assay, where the TGR5 is either expressed at a physiological level or overexpressed).

In one aspect, the present invention relates to a compound of formula I, II, III, or IV, wherein the compound induces apoptosis.

In one aspect, the present invention relates to a compound of formula I, II, III, or IV, wherein the compound shows no cytotoxic effect on human HepG2 liver cells (e.g., as measured by an LDH release assay or an intracellular ATP assay).

In one aspect, the present invention relates to a compound of formula I, II, III, or IV, wherein the compound does not inhibit one or more CYP450 isoforms selected from CYP1A2, CYP3A4 (green substrate), CYP3A4 (blue substrate), CYP2C9, CYP2C19, CYP2D6, and CYP2E1. For example, the compounds of the invention have an $IC_{50}$ greater than 10 μM as measured by CPY450 inhibition assay.

In one aspect, the present invention relates to a compound of formula I, II, III, or IV, wherein the compound does not inhibit the human ERG potassium channel.

In one aspect, the present invention relates to a method of synthesizing a compound of the invention, or a pharmaceutically acceptable salt, solvate, or amino acid conjugate thereof.

In one aspect, the present invention relates to a kit containing one or more compounds of the invention, or a pharmaceutically acceptable salt, solvate, or amino acid conjutate thereof. In one aspect, the kit further contains a pharmaceutically acceptable ingredient.

In one aspect, the present invention relates to a pharmaceutical composition comprising a compound of the invention and a pharmaceutically acceptable excipient.

One technical problem to be solved by the present invention is the identification of novel compounds that are agonists of the nuclear hormone farnesoid X receptor (FXR), which represents an attractive target for the treatment of metabolic and chronic liver diseases. It is well known that natural bile acids modulate not only several nuclear hormone receptors, but are also agonists for the G protein-coupled receptor (GPCR) TGR5. Selectivity can be a problem for drug compounds directed to modulating a nuclear hormone receptor. It is therefore an objective of the present invention to provide a compound that is a specific FXR agonist, for example, a compound that shows no activity against other nuclear receptors or a compound that does not activate the bile acid GPCR TGR5. Other problems in the development of a drug compound include a non-suitable pharmacokinetic profile, safety issues such as toxicity (e.g., liver) and undesirable drug-drug interactions. Accordingly, further objectives of the present invention are to provide compounds that do not suffer from the aforementioned technical problems, i.e., a compound that has a suitable pharmacokinetic profile, a compound that does not exert a cytotoxic effect on cells, a compound that does not inhibit cytochrome P450 enzymes, and/or a compound that does not inhibit hERG.

The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used (unless expressly stated otherwise).

The general chemical terms used throughout have their usual meanings. For example, the term alkyl refers to a branched or unbranched saturated hydrocarbon group. The term "n-alkyl" refers to an unbranched alkyl group. The term "$C_x$-$C_y$ alkyl" refers to an alkyl group having between x and y carbon atoms, inclusively, in the branched or unbranched hydrocarbon group. By way of illustration, but without limitation, the term "$C_1$-$C_8$ alkyl" refers to a straight chain or branched hydrocarbon moiety having 1, 2, 3, 4, 5, 6, 7, or 8 carbon atoms. "$C_1$-$C_6$" refers to a straight chain or branched hydrocarbon moiety having 1, 2, 3, 4, 5, or 6 carbon atoms. "$C_1$-$C_4$ alkyl" refers to a straight chain or branched hydrocarbon moiety having 1, 2, 3, or 4 carbon atoms, including methyl, ethyl, n-propyl, isopropyl, n-butyl, isobutyl, sec-butyl, and tert-butyl. The term "$C_1$-$C_4$ n-alkyl" refers to straight chain hydrocarbon moieties that have from 1, 2, 3, or 4 carbon atoms including methyl, ethyl, n-propyl, and n-butyl. The term "$C_3$-$C_6$ cycloalkyl" refers to cyclopropyl, cyclobutyl, cyclopentyl, and cyclohexyl. The term "$C_3$-$C_7$ cycloalkyl" also includes cycloheptyl. The term "$C_3$-$C_8$ cycloalkyl" also includes cyclooctyl. Cycloalkylalkyl refers to cycloalkyl moieties linked through an alkyl linker chain, as for example, but without limitation, cyclopropylmethyl, cyclopropylethyl, cyclopropylpropyl, cyclopropylbutyl, cyclobutylmethyl, cyclobutylethyl, cyclobutylpropyl, cyclopentylmethyl, cyclopentylethyl, cyclopentylpropyl, cyclohexylmethyl, cyclohexylethyl, and cyclohexylpropyl. Each alkyl, cycloalkyl, and cycloalkylalkyl group may be optionally substituted as specified herein.

The term "$C_4$-$C_8$ cycloalkenyl" refers cyclobutenyl, cyclopentyl, cyclohexenyl, cycloheptenyl, and cyclooctenyl rings having one or more sites of unsaturation, e.g., one or more double bonds.

The term "halogen" refers to fluoro, chloro, bromo, or iodo.

The term "hydroxyl" means OH.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds unless otherwise specified. In a broad aspect, the permissible substituents include acyclic and cyclic, branched and unbranched, carbocyclic and heterocyclic, aromatic and nonaromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "pharmaceutical" or "pharmaceutically acceptable" when used herein as an adjective, means substantially non-toxic and substantially non-deleterious to the recipient.

By "pharmaceutical formulation" it is further meant that the carrier, solvent, excipient, and salt must be compatible with the active ingredient of the formulation (e.g., a compound of the invention). It is understood by those of ordinary skill in this art that the terms "pharmaceutical formulation" and "pharmaceutical composition" are generally interchangeable, and they are so used for the purposes of this application.

Suitable pharmaceutically acceptable salts according to the invention will be readily determined by one skilled in the art and will include, for example, basic salts such as alkali or alkaline-earth metallic salts made from aluminium, calcium, lithium, magnesium, potassium, sodium, and zinc or organic salts made from N,N'-dibenzylethylenediamine, chlorprocaine, choline, diethanolamine, ethylenediamine, meglumine (N-methylglucamine), and procaine. Salts with pharmaceutically acceptable amines such as lysine, arginine, tromethamine, triethylamine and the like can also be used. Such salts of the compounds of the invention may be prepared using conventional techniques, from the compound of the invention by reacting, for example, the appropriate base with the compound of the invention.

When used in medicine, the salts of a compound of the invention should be pharmaceutically acceptable, but pharmaceutically unacceptable salts may conveniently be used to prepare the corresponding free base or pharmaceutically acceptable salts thereof.

As used herein, the term "amino acid conjugate" refers to a conjugate of a compound of the invention with any suitable amino acid. In one aspect, such suitable amino acid conjugate of a compound of the invention will have the added advantage of enhanced integrity in bile or intestinal fluids. The present invention encompasses the glycine and taurine conjugates of any of the compounds of the invention. For example, the glycine and the taurine conjugates of a compound of formula I have the following formula:

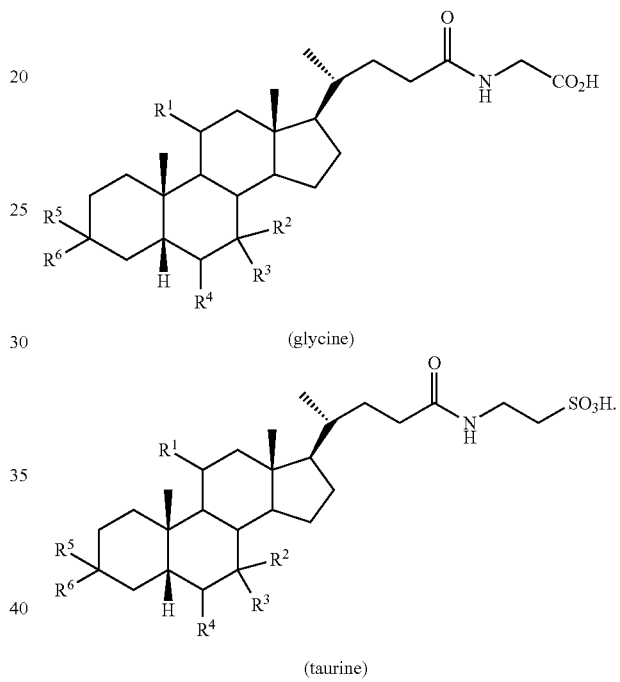

In one aspect, the glycine and taurine conjuates of a compound of the invention may be a pharmaceutically acceptable salt thereof. The amino acid conjugates of compounds of the invention can be prepared according to methods known in the art. For example, the free acid can be coupled to the glycine or taurine amino acid using standard peptide coupling conditions.

In one aspect, the sodium salt of the taurine conjugate of Compound 100 can be prepared as follows.

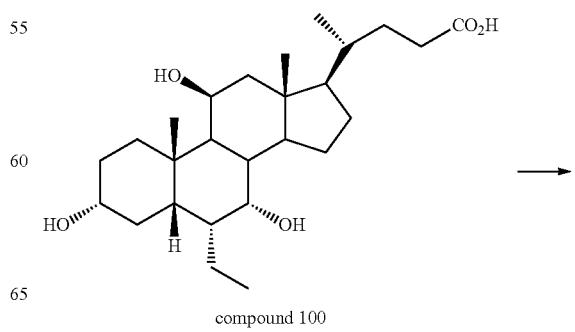

compound 100

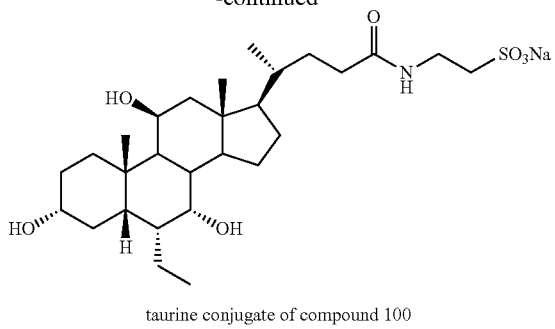

taurine conjugate of compound 100

Compound 100 is treated with a base (e.g., Et₃N) and taurine in a polar protic solvent (e.g., EtOH). The resulting mixture can be treated with a coupling reagent (e.g., DMT-MM (4-(4,6-Dimethoxy-1,3,5-triazin-2-yl)-4-methylmorpholinium chloride)). The reaction mixture can be concentrated and dissolved in a base (e.g., 3% w/v aqueous solution of NaOH). The resulting reaction mixture can be extracted with an organic solvent (e.g., AcOEt). The aqueous phase can be concentrated and filtered on a silica pad, eluting first with, e.g., H₂O (until neutral pH) and then with, e.g., H₂O/MeOH 80:20 v/v to give the taurine conjugate of Compound 100. Suitable amino acids include but are not limited to glycine and taurine.

Some of the compounds of the present invention may exist in unsolvated as well as solvated forms such as, for example, hydrates.

The present invention provides methods for the synthesis of the compounds of invention described herein. The present invention also provides detailed methods for the synthesis of various disclosed compounds of the invention according to the following schemes as shown in the examples.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester or prodrug thereof.

Compounds of the invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's Advanced Organic Chemistry: Reactions, Mechanisms, and Structure, 5th edition, John Wiley & Sons: New York, 2001; and Greene, T. W., Wuts, P. G. M., Protective Groups in Organic Synthesis, 3rd edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present invention.

All the abbreviations used in this application are found in "Protective Groups in Organic Synthesis" by John Wiley & Sons, Inc, or the MERCK INDEX by MERCK & Co., Inc, or other chemistry books or chemicals catalogs by chemicals vendor such as Aldrich, or according to usage know in the art.

Scheme 1

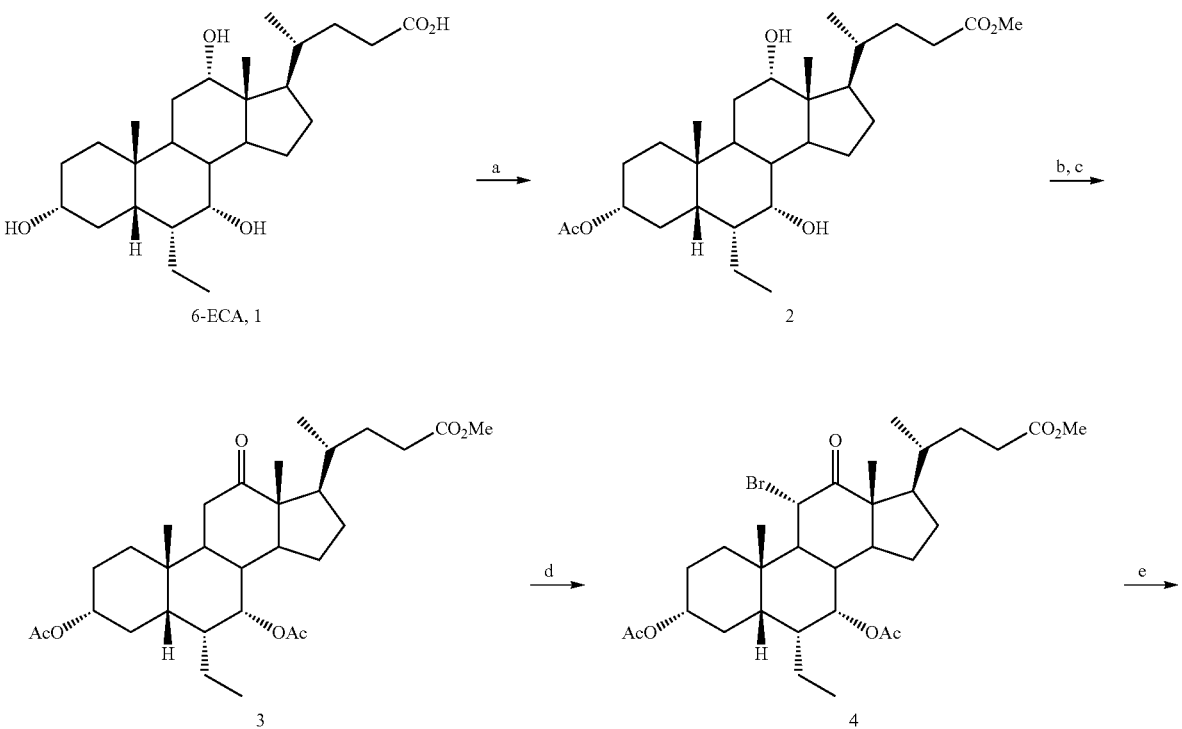

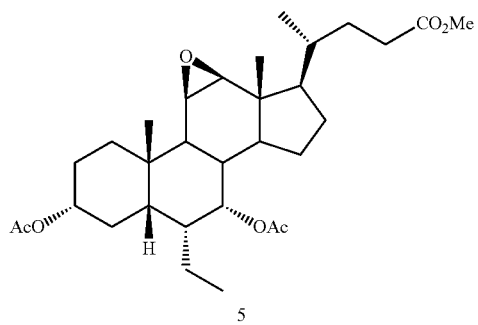

5

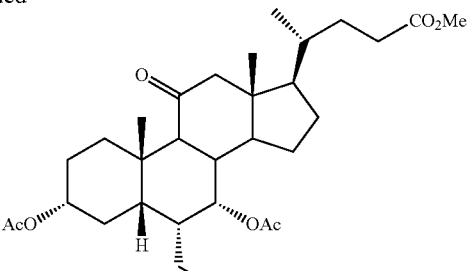

6

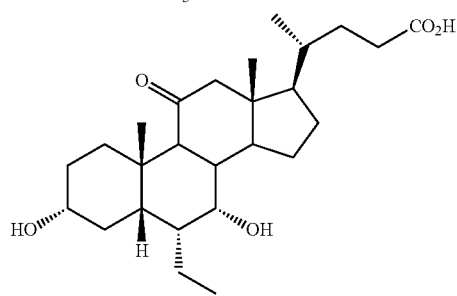

7

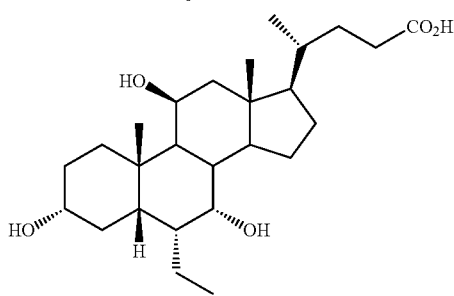

compound 100

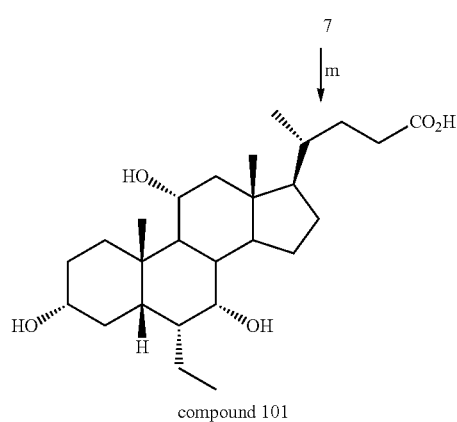

compound 101

Reagents and conditions: a) 1) MeOH, p-TSA, ultrasound, 3 h, quantitative; 2) Ac$_2$O, NaHCO$_3$, THF, reflux 12 h, 85%; b) PCC, CH$_2$Cl$_2$, 6 h, 62%; c) Ac$_2$O, Bi(OTf)$_3$, CH$_2$Cl$_2$, 1 h, 91%; d) Br$_2$, Benzene, 30° C. overnight, 74%; e) NaBH$_4$, NaOAc, Pyr, r.t. 2 days, 80%; f) HI 57%, AcOH, r.t. 30 min; g) CrO$_3$, AcOH, r.t. 45 min; h) Zn dust, NaOAc, reflux 20 min; i) NaOH 2M, MeOH, r.t. overnight, 65% from compound 5; 1) NaBH$_4$, THF/H$_2$O 4:1, 70%; m) Na(s), sec-BuOH, 50° C., 70%.

The synthesis is based on the use of 6α-ethyl-cholic acid (6-ECA, 1) as starting material which was prepared using methods known in the art. 6-ECA (1) was treated with p-TSA in MeOH under ultrasound irradiation to give the corresponding methyl ester, which was selectively protected at the C3 position by refluxing with Ac$_2$O in the present of NaHCO$_3$ in THF to afford compound 2. Treating compound 2 with PCC in CH$_2$Cl$_2$ at room temperature followed by treatment with Ac$_2$O, Bi(OTf)$_3$ in CH$_2$Cl$_2$ at room temperature afforded the intermediate methyl 3α,7α-diacetoxy-12-oxo-5β-cholan-24-oate (compound 3; about 48% from compound 2).

Treatment of compound 3 with Br$_2$ in benzene for e.g., 12 h yielded compound 4. Reaction of compound 4 with NaBH$_4$ and NaOAc in freshly distilled pyridine gave the corresponding 11β-12β epoxide (compound 5), in about 59% yield after silica gel purification. The reaction of compound 5 with HI in AcOH at room temperature afforded the halohydrine intermediate which were then oxidized at C11 position with CrO$_3$ in AcOH to generate compound 6. Reaction of compound 6 with Zn dust in boiling AcOH and alkali hydrolysis (NaOH/MeOH) afforded 3α,7α-hydroxy-12-keto-5b-cholan-24-oic acid (compound 7; about 65% yield from compound 5).

Compound 7 was stereoselectively reduced at the C11-carbonyl using NaBH$_4$ in a mixture of THF/H$_2$O=(4:1, v/v) to give 3α,7α, 11β-trihydroxy-6α-ethyl-5β-cholan-24-oic acid (Compound 100; about 27% from compound 3), after chromatographic purification to afford Compound 100. Alternatively, compound 7 was reduced with sodium in sec-BuOH at 50° C. to give Compound 101 (about 70% yield), after purification.

"Solvate" means a solvent addition form that contains either a stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; when the solvent is alcohol, the solvate formed is an alcoholate. Hydrates are formed by the combination of one or more molecules of water with one of the substances in which the water retains its molecular state as $H_2O$, such combination being able to form one or more hydrate.

The term "suitable solvent" refers to any solvent, or mixture of solvents, inert to the ongoing reaction that sufficiently solubilizes the reactants to afford a medium within which to effect the desired reaction.

The compounds described herein can have asymmetric centers. Compounds of the present invention containing an asymmetrically substituted atom can be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and can be isolated as a mixture of isomers or as separate isomeric forms. All chiral, diastereomeric, racemic, and geometric isomeric forms of a structure are intended, unless specific stereochemistry or isomeric form is specifically indicated. All processes used to prepare compounds of the present invention and intermediates made therein are considered to be part of the present invention. All tautomers of shown or described compounds are also considered to be part of the present invention. Furthermore, the invention also includes metabolites of the compounds described herein.

The invention also comprehends isotopically-labeled compounds, which are identical to those recited in the formulae of the invention, but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, fluorine, such as $^3H$, $^{11}C$, $^{14}C$, $^2H$, and $^{18}F$.

Compounds of the present invention and pharmaceutically acceptable salts, solvates or amino acid conjugates thereof that contain the aforementioned isotopes and/or other isotopes of other atoms are within the scope of the present invention. Isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography). PET is useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of this invention can generally be prepared through techniques known in the art, such as by carrying out the procedures disclosed in the Schemes and/or in the Examples below, by substituting a readily available isotopically labeled reagent for a non-isotopically labeled reagent. In one embodiment, the compounds of the invention, salts, hydrates, solvates, or amino acid conjugates thereof are not isotopically labelled.

When any variable (e.g., $R^x$) occurs more than one time in any constituent or formula for a compound, its definition at each occurrence is independent of its definition at every other occurrence. Thus, for example, if a group is shown to be substituted with one or more $R^x$ moieties, then $R^x$ at each occurrence is selected independently from the definition of $R^x$. Also, combinations of substituents and/or variables are permissible, but only if such combinations result in stable compounds within a designated atom's normal valency.

As used herein, the term "treat," "treating," or "treatment" is meant decreasing the symptoms, markers, and/or any negative effects of a condition in any appreciable degree in a subject who currently has the condition. In some embodiments, treatment may be administered to a subject who exhibits only early signs of the condition for the purpose of decreasing the risk of developing the disease or condition.

As used herein, the term "prevent," "prevention," or "preventing" refers to any method to partially or completely prevent or delay the onset of one or more symptoms or features of a disease, disorder, and/or condition. Prevention may be administered to a subject who does not exhibit signs of a disease or condition.

As used herein, "subject" means a human or animal (in the case of an animal, more typically a mammal). In one aspect, the subject is a human. Such subject can be considered to be in need of treatment with an FXR agonist.

As used herein, "unsaturated" refers to compounds or structures having at least one degree of unsaturation (e.g., at least one double or triple bond).

As used herein, the term "a compound of the invention" includes a compound of any of formulae I, II, III, or IV, or any compound explicitly disclosed herein.

As used herein, farnesoid X receptor or FXR refers to all mammalian forms of such receptor including, for example, alternative splice isoforms and naturally occurring isoforms (see, e.g., Huber et al., *Gene* 290:35-43 (2002)). Representative FXR species include, without limitation rat FXR (Gen Bank Accession No. NM_021745), mouse FXR (Genbank Accession No. NM_009108), and human FXR (GenBank Accession No. NM_005123).

As used herein, Compound A is

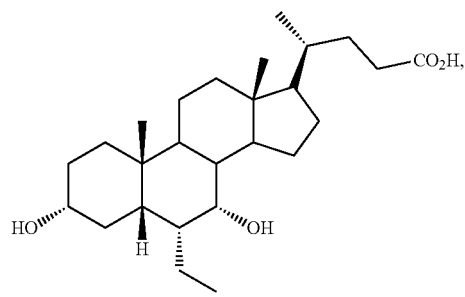

which is also known as obeticholic acid, INT-747, 6ECDCA, 6-alpha-ethyl chenodeoxycholic acid, or 6α-ethyl-3α,7α-dihydroxy-5β-cholan-24-oic acid.

As used herein, Compound B is

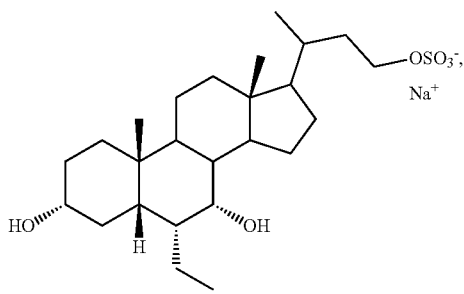

which is also known as INT-767 or 6α-ethyl-3α,7α,23-trihydroxy-24-nor-5β-cholan-23-sulfate sodium salt.

As used herein, Compound C is

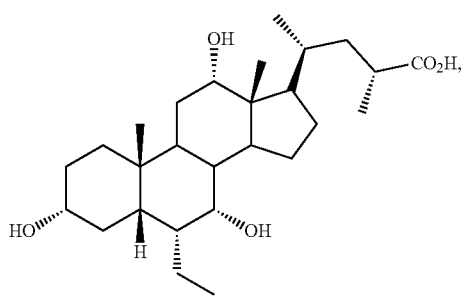

which is also known as INT-777 or 6α-ethyl-23(S)-methyl-3α,7α,12α trihydroxy-5β-cholan-24-oic acid.

As used herein, Compound D is

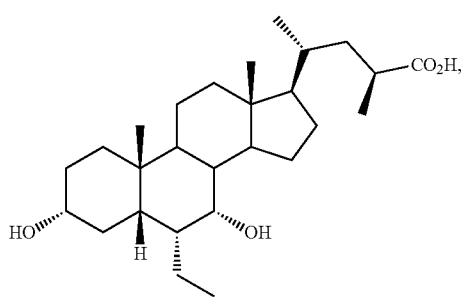 [SMILES: CC[C@H]1[C@@H](O)C2C3CC[C@H]([C@H](C)C[C@H](C)C(=O)O)[C@@]3(C)CCC2[C@@]2(C)CC[C@@H](O)C[C@@H]12]

which is also known as 6α-ethyl-23(R)-methyl chenodeoxycholic acid, and S-EMCDCA.

As used herein, Compound E is

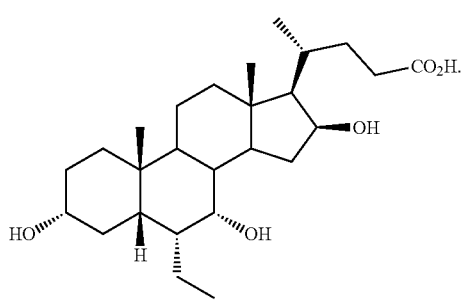 [SMILES: CC[C@H]1[C@@H](O)C2C3C[C@H](O)[C@H]([C@H](C)CCC(=O)O)[C@@]3(C)CCC2[C@@]2(C)CC[C@@H](O)C[C@@H]12]

As used herein, cholic acid is

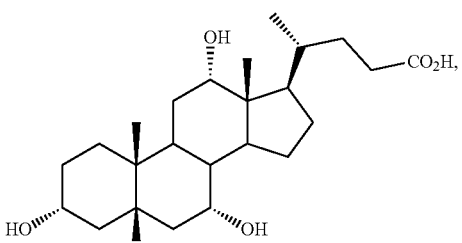

which is also known as CA.

As used herein, chenodeoxycholic acid is

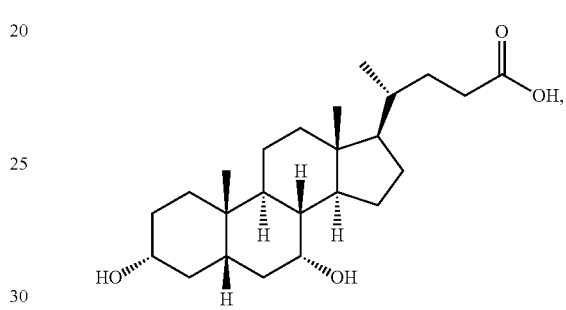

which is also known as CDCA.

As used herein, ursodeoxycholic acid is

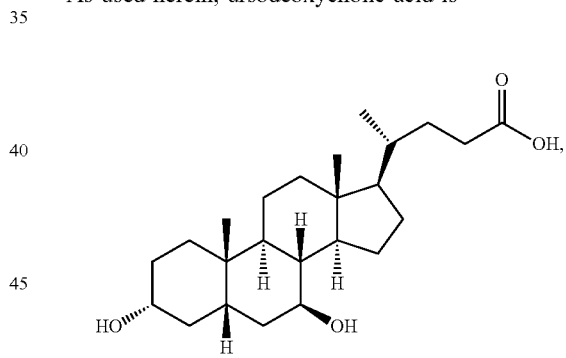

which is also known as UDCA.

As used herein, taurochenodeoxycholic acid is

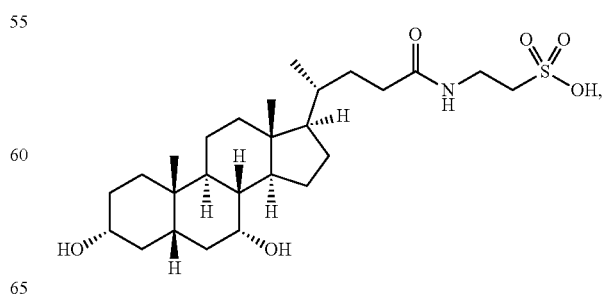

which is also known asn TCDCA.

As used herein, tauroursodeoxycholic acid is

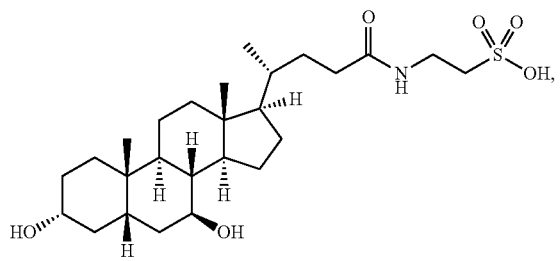

which is also known as TUDCA.

As used herein, lithocholic acid is

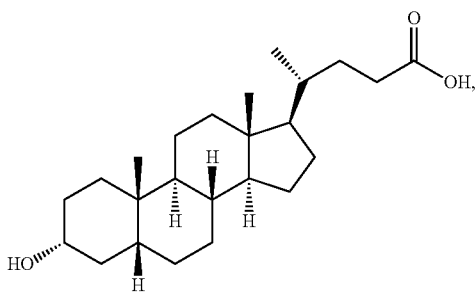

which is also known as LCA.

Methods of the Invention

Compounds of the invention are useful in therapy in subjects such as mammals, including humans. In particular, compounds of the invention are useful in a method of treating or preventing a disease or condition in a subject comprising administering to the subject in need thereof an effective amount of a compound of the invention or a pharmaceutically acceptable salt, solvate, or amino acid conjugate thereof. In one aspect, the disease or condition is FXR-mediated (e.g., FXR plays a role in the initiation or progress of the disease or condition). In one aspect, the disease or condition is mediated by decreased FXR activity. In one aspect, the disease or condition is selected from cardiovascular disease, chronic liver disease, lipid disorder, gastrointestinal disease, renal disease, metabolic disease, cancer, and neurological disease.

In one aspect, the invention relates to a method of treating or preventing cardiovascular disease in a subject, comprising administereing to the subject in need thereof an effective amount of a compound of the invention or a pharmaceutically acceptable salt, solvate, or amino acid conjugate thereof. In one aspect, the invention relates to a method of treating cardiovascular disease. In one aspect, the invention relates to a method of preventing cardiovascular disease. In one aspect, cardiovascular disease selected from atherosclerosis, arteriosclerosis, dyslipidemia, hypercholesteremia, hyperlipidemia, hyperlipoproteinemia, and hypertriglyceridemia.

The term "hyperlipidemia" refers to the presence of an abnormally elevated level of lipids in the blood. Hyperlipidemia can appear in at least three forms: (1) hypercholesterolemia, i.e., an elevated cholesterol level; (2) hypertriglyceridemia, i.e., an elevated triglyceride level; and (3) combined hyperlipidemia, i.e., a combination of hypercholesterolemia and hypertriglyceridemia.

The term "dyslipidemia" refers to abnormal levels of lipoproteins in blood plasma including both depressed and/or elevated levels of lipoproteins (e.g., elevated levels of LDL, VLDL and depressed levels of HDL).

In one aspect, the invention relates to a method selected from reducing cholesterol levels or modulating cholesterol metabolism, catabolism, absorption of dietary cholesterol, and reverse cholesterol transport in a subject, comprising administering to the subject in need thereof an effective amount of a compound of the invention or a pharmaceutically acceptable salt, solvate, or amino acid conjugate thereof.

In one aspect, the invention relates to a method of treating or preventing a disease affecting cholesterol, triglyceride, or bile acid levels in a subject, comprising administering to the subject in need thereof an effective amount of a compound of the invention or a pharmaceutically acceptable salt, solvate, or amino acid conjugate thereof.

In one aspect, the invention relates to a method of lowering triglycerides in a subject, comprising administering to the subject in need thereof an effective amount of a compound of the invention or a pharmaceutically acceptable salt, solvate, or amino acid conjugate thereof.

In one aspect, the invention relates to a method of treating or preventing a disease state associated with an elevated cholesterol level in a subject, comprising administering to the subject in need thereof an effective amount of a compound of the invention or a pharmaceutically acceptable salt, solvate, or amino acid conjugate thereof. In one aspect, the invention relates to a method of treating a disease state associated with an elevated cholesterol level in a subject. In one aspect, the invention relates to a method of preventing a disease state associated with an elevated cholesterol level in a subject. In one aspect, the disease state is selected from coronary artery disease, angina pectoris, carotid artery disease, strokes, cerebral arteriosclerosis, and xanthoma.

In one aspect, the invention relates to a method of treating or preventing a lipid disorder in a subject, comprising administereing to the subject in need thereof an effective amount of a compound of the invention or a pharmaceutically acceptable salt, solvate, or amino acid conjugate thereof. In one aspect, the invention relates to a method of treating a lipid disorder. In one aspect, the invention relates to a method of preventing a lipid disorder.

Lipid disorders are the term for abnormalities of cholesterol and triglycerides. Lipid abnormalities are associated with an increased risk for vascular disease, and especially heart attacks and strokes. Abnormalities in lipid disorders are a combination of genetic predisposition as well as the nature of dietary intake. Many lipid disorders are associated with being overweight. Lipid disorders may also be associated with other diseases including diabetes, the metabolic syndrome (sometimes called the insulin resistance syndrome), underactive thyroid or the result of certain medications (such as those used for anti-rejection regimens in people who have had transplants).

In one aspect, the invention relates to a method of treating or preventing one or more symptoms of disease affecting lipid metabolism (i.e., lipodystrophy) in a subject, comprising administering to the subject in need thereof an effective amount of a compound of the invention or a pharmaceutically acceptable salt, solvate, or amino acid conjugate thereof. In one aspect, the invention relates to a method of treating one or more symptoms of a disease affecting lipid metabolism. In one aspect, the invention relates to a method of preventing one or more symptoms of a disease affecting lipid metabolism.

In one aspect, the invention relates to a method of decreasing lipid accumulation in a subject, comprising administering to the subject in need thereof an effective amount of a compound of the invention or a pharmaceutically acceptable salt, solvate, or amino acid conjugate thereof.

In one aspect, the invention relates to a method of treating or preventing chronic liver disease in a subject, comprising administereing to the subject in need thereof an effective amount of a compound of the invention or a pharmaceutically acceptable salt, solvate, or amino acid conjugate thereof. In one aspect, the invention relates to a method of treating chronic liver disease. In one aspect, the invention relates to a method of preventing chronic liver disease. In one aspect, the chronic liver disease is selected from primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, and alpha 1-antitrypsin deficiency.

In one aspect, the invention relates to a method of treating or preventing one or more symptoms of cholestasis, including complications of cholestasis in a subject, comprising administering to the subject in need thereof an effective amount of a compound of the invention or a pharmaceutically acceptable salt, solvate, or amino acid conjugate thereof. In one aspect, the invention relates to a method of treating one or more symptoms of cholestasis. In one aspect, the invention relates to preventing one or more symptoms of cholestasis.

Cholestasis is typically caused by factors within the liver (intrahepatic) or outside the liver (extrahepatic) and leads to the accumulation of bile salts, bile pigment bilirubin, and lipids in the blood stream instead of being eliminated normally. Intrahepatic cholestasis is characterized by widespread blockage of small ducts or by disorders, such as hepatitis, that impair the body's ability to eliminate bile. Intrahepatic cholestasis may also be caused by alcoholic liver disease, primary biliary cirrhosis, cancer that has spread (metastasized) from another part of the body, primary sclerosing cholangitis, gallstones, biliary colic and acute cholecystitis. It can also occur as a complication of surgery, serious injury, cystic fibrosis, infection, or intravenous feeding or be drug induced. Cholestasis may also occur as a complication of pregnancy and often develops during the second and third trimesters.

Extrahepatic cholestasis is most often caused by choledocholithiasis (Bile Duct Stones), benign biliary strictures (non-cancerous narrowing of the common duct), cholangiocarcinoma (ductal carcinoma) and pancreatic carcinoma. Extrahepatic cholestasis can occur as a side effect of many medications.

A compound of the invention may be used for treating or preventing one or more symptoms of intrahepatic or extrahepatic cholestasis, including without limitation, biliary artesia, obstetric cholestasis, neonatal cholestasis, drug induced cholestasis, cholestasis arising from Hepatitis C infection, chronic cholestatic liver disease such as primary biliary cirrhosis (PBC), and primary sclerosing cholangitis (PSC).

In one aspect, the invention relates to a method of enhancing liver regeneration in a subject, comprising administering to the subject in need thereof an effective amount of a compound of the invention or a pharmaceutically acceptable salt, solvate, or amino acid conjugate thereof. In one aspect, the method is enhancing liver regeneration for liver transplantation.

In one aspect, the invention relates to a method of treating or preventing fibrosis in a subject, comprising administering to the subject in need thereof an effective amount of a compound of the invention or a pharmaceutically acceptable salt, solvate, or amino acid conjugate thereof. In one aspect, the invention relates to a method of treating fibrosis. In one aspect, the invention relates to a method of preventing fibrosis.

Accordingly, as used herein, the term fibrosis refers to all recognized fibrotic disorders, including fibrosis due to pathological conditions or diseases, fibrosis due to physical trauma ("traumatic fibrosis"), fibrosis due to radiation damage, and fibrosis due to exposure to chemotherapeutics. As used herein, the term "organ fibrosis" includes but is not limited to liver fibrosis, fibrosis of the kidneys, fibrosis of lung, and fibrosis of the intestine. "Traumatic fibrosis" includes but is not limited to fibrosis secondary to surgery (surgical scarring), accidental physical trauma, burns, and hypertrophic scarring.

As used herein, "liver fibrosis" includes liver fibrosis due to any cause, including but not limited to virally-induced liver fibrosis such as that due to hepatitis B or C virus; exposure to alcohol (alcoholic liver disease), certain pharmaceutical compounds including but not limited to methotrexate, some chemotherapeutic agents, and chronic ingestion of arsenicals or vitamin A in megadoses, oxidative stress, cancer radiation therapy or certain industrial chemicals including but not limited to carbon tetrachloride and dimethylnitrosamine; and diseases such as primary biliary cirrhosis, primary sclerosing colangitis, fatty liver, obesity, non-alcoholic steatohepatitis, cystic fibrosis, hemochromatosis, auto-immune hepatitis, and steatohepatitis. Current therapy in liver fibrosis is primarily directed at removing the causal agent, e.g., removing excess iron (e.g., in the case of hemochromatosis), decreasing viral load (e.g., in the case of chronic viral hepatitis), or eliminating or decreasing exposure to toxins (e.g., in the case of alcoholic liver disease). Anti-inflammatory drugs such as corticosteroids and colchicine are also known for use in treating inflammation that can lead to liver fibrosis.

As is known in the art, liver fibrosis may be clinically classified into five stages of severity (S0, S1, S2, S3, and S4), usually based on histological examination of a biopsy specimen. S0 indicates no fibrosis, whereas S4 indicates cirrhosis. While various criteria for staging the severity of liver fibrosis exist, in general early stages of fibrosis are identified by discrete, localized areas of scarring in one portal (zone) of the liver, whereas later stages of fibrosis are identified by bridging fibrosis (scarring that crosses zones of the liver).

In one aspect, the invention relates to a method of treating or preventing organ fibrosis in a subject, comprising administering to the subject in need thereof an effective amount of a compound of the invention or a pharmaceutically acceptable salt, solvate, or amino acid conjugate thereof. In one aspect, the fibrosis is liver fibrosis.

In one aspect, the invention relates to a method of treating or preventing gastrointestinal disease in a subject, comprising administereing to the subject in need thereof an effective amount of a compound of the invention or a pharmaceutically acceptable salt, solvate, or amino acid conjugate thereof. In one aspect, the invention relates to a method of treating gastrointestinal disease. In one aspect, the invention relates to a method of preventing gastrointestinal disease. In one aspect, the gastrointestinal disease is selected from inflammatory bowel disease (IBD), irritable bowel syndrome (IBS), bacterial overgrowth, malabsorption, post-radiation colitis, and microscopic colitis. In one aspect, the inflammatory bowel disease is selected from Crohn's disease and ulcerative colitis.

In one aspect, the invention relates to a method of treating or preventing renal disease in a subject, comprising administereing to the subject in need thereof an effective amount of a compound of the invention or a pharmaceutically acceptable salt, solvate, or amino acid conjugate thereof. In one aspect, the invention relates to a method of treating renal disease. In one aspect, the invention relates to a method of preventing renal disease. In one aspect, the renal disease is selected from diabetic nephropathy, focal segmental glomerulosclerosis (FSGS), hypertensive nephrosclerosis, chronic glomerulonephritis, chronic transplant glomerulopathy, chronic interstitial nephritis, and polycystic kidney disease.

In one aspect, the invention relates to a method of treating or preventing metabolic disease in a subject, comprising administereing to the subject in need thereof an effective amount of a compound of the invention or a pharmaceutically acceptable salt, solvate, or amino acid conjugate thereof. In one aspect, the invention relates to a method of treating renal disease. In one aspect, the invention relates to a method of preventing renal disease. In one aspect, the metabolic disease is selected from insulin resistance, hyperglycemia, diabetes mellitus, diabesity, and obesity. In one aspect, the diabetes mellitus is type I diabetes. In one aspect, the diabetes mellitus is type II diabetes.

Diabetes mellitus, commonly called diabetes, refers to a disease or condition that is generally characterized by metabolic defects in production and utilization of glucose which result in the failure to maintain appropriate blood sugar levels in the body.

In the case of type II diabetes, the disease is characterized by insulin resistance, in which insulin loses its ability to exert its biological effects across a broad range of concentrations. This resistance to insulin responsiveness results in insufficient insulin activation of glucose uptake, oxidation and storage in muscle and inadequate insulin repression of lipolysis in adipose tissue and of glucose production and secretion in liver. The resulting condition is elevated blood glucose, which is called "hyperglycemia". Uncontrolled hyperglycemia is associated with increased and premature mortality due to an increased risk for microvascular and macrovascular diseases, including retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys), hypertension, cerebrovascular disease and coronary heart disease. Therefore, control of glucose homeostasis is a critically important approach for the treatment of diabetes.

Insulin resistance has been hypothesized to unify the clustering of hypertension, glucose intolerance, hyperinsulinemia, increased levels of triglyceride and decreased HDL cholesterol, and central and overall obesity. The association of insulin resistance with glucose intolerance, an increase in plasma triglyceride and a decrease in high-density lipoprotein cholesterol concentrations, hypertension, hyperuricemia, smaller denser low-density lipoprotein particles, and higher circulating levels of plasminogen activator inhibitor-1, has been referred to as "Syndrome X". Accordingly, methods of treating or preventing any disorders related to insulin resistance including the cluster of disease states, conditions or disorders that make up "Syndrome X" are provided. In one aspect, the invention relates to a method of treating or preventing metabolic syndrome in a subject, comprising administering to the subject in need thereof an effective amount of a compound of the invention or a pharmaceutically acceptable salt, solvate, or amino acid conjugate thereof. In one aspect, the invention relates to a method of treating metabolic syndrome. In one aspect, the invention relates to a method of preventing metabolic syndrome.

In one aspect, the invention relates to a method of treating or preventing cancer in a subject, comprising administereing to the subject in need thereof an effective amount of a compound of the invention or a pharmaceutically acceptable salt, solvate, or amino acid conjugate thereof. In one aspect, the invention relates to a method of treating cancer. In one aspect, the invention relates to a method of preventing cancer. In one aspect, the cancer is colorectal cancer.

In one aspect, the invention relates to a method of treating or preventing gallstones in a subject, comprising administering to the subject in need thereof an effective amount of a compound of the invention or a pharmaceutically acceptable salt, solvate, or amino acid conjugate thereof. In one aspect, the invention relates to a method of treating gallstones. In one aspect, the invention relates to a method of preventing gallstones.

A gallstone is a crystalline concretion formed within the gallbladder by accretion of bile components. These calculi are formed in the gallbladder but may distally pass into other parts of the biliary tract such as the cystic duct, common bile duct, pancreatic duct, or the ampulla of Vater. Rarely, in cases of severe inflammation, gallstones may erode through the gallbladder into adherent bowel potentially causing an obstruction termed gallstone ileus. Presence of gallstones in the gallbladder may lead to acute cholecystitis, an inflammatory condition characterized by retention of bile in the gallbladder and often secondary infection by intestinal microorganisms, predominantly *Escherichia coli* and *Bacteroides* species. Presence of gallstones in other parts of the biliary tract can cause obstruction of the bile ducts, which can lead to serious conditions such as ascending cholangitis or pancreatitis.

In one aspect, the invention relates to a method of treating or preventing cholesterol gallstone disease in a subject, comprising administering to the subject in need thereof an effective amount of a compound of the invention or a pharmaceutically acceptable salt, solvate, or amino acid conjugate thereof. In one aspect, the invention relates to a method of treating cholesterol gallstone disease. In one aspect, the invention relates to a method of preventing cholesterol gallstone disease.

In one aspect, the invention relates to a method of treating or preventing neurological disease in a subject, comprising administering to the subject in need thereof an effective amount of a compound of the invention or a pharmaceutically acceptable salt, solvate, or amino acid conjugate thereof. In one aspect, the invention relates to a method of treating neurological disease. In one aspect, the invention relates to a method of preventing neurological disease. In one aspect, the neurological disease is stroke.

In one aspect, the invention relates to a method as decribed herein and further wherein, the compound is administered by a route selected from oral, parenteral, intramuscular, intranasal, sublingual, intratracheal, inhalation, ocular, vaginal, rectal, and intracerebroventricular. In one aspect, the route is oral.

In one aspect, the compound utiltized in one or more of the methods described herein is an FXR agonist. In one aspect, the compound is a selective FXR agonist. In one aspect, the compound does not activate TGR5. In one aspect, the compound does not activate other nuclear receptors involved in metabolic pathways (e.g., as measured by an AlphaScreen assay). In one aspect, such other nuclear receptors involved in metabolic pathways are selected from LXRβ, PXR, CAR, PPARα, PPARδ, RARα, VDR, TR, PR, RXR, GR, and ER. In one aspect, the compound induces apoptosis.

In one aspect, the invention relates to a method of regulating the expression level of one or more genes involved in bile acid homeostasis.

In one aspect, the invention relates to a method of down regulating the expression level of one or more genes selected from CYP7α1 and SREBP-1C in a cell by administering to the cell a compound of the invention. In one aspect, the invention relates to a method of up regulating the expression level of one or more genes selected from OSTα, OSTβ, BSEP, SHP, UGT2B4, MRP2, FGF-19, PPARγ, PLTP, APOCII, and PEPCK in a cell by administering to the cell a compound of the invention.

The invention also relates to the manufacture of a medicament for treating or preventing a disease or condition (e.g., a disease or condition mediated by FXR), wherein the medicament comprises a compound of the invention or a pharmaceutically acceptable salt, solvate, or amino acid conjugate thereof. In one aspect, the invention relates to the manufacture of a medicament for treating or preventing any one of the diseases or conditions described herein above, wherein the medicament comprises a compound of the invention or a pharmaceutically acceptable salt, solvate, or amino acid conjugate thereof.

The invention also relates to a composition for use in a method for treating or preventing a disease or condition (e.g., a disease or condition mediated by FXR), wherein the composition comprises a compound of the invention or a pharmaceutically acceptable salt, solvate, or amino acid conjugate thereof. In one aspect, the invention relates to a composition for use in a method for treating or preventing any one of the diseases or conditions described herein above, wherein the composition comprises a compound of the invention or a pharmaceutically acceptable salt, solvate, or amino acid conjugate thereof.

Formulations

The methods of the invention comprise the step of administering an effective amount of a compound of the invention. As used herein, the term an "effective amount" refers to an amount of a compound of the invention which is sufficient to achieve the stated effect. Accordingly, an effective amount of a compound of the invention used in a method for the prevention or treatment of FXR mediated diseases or conditions will be an amount sufficient to prevent or treat the FXR mediated disease or condition.

Similarly, an effective amount of a compound of the invention for use in a method for the prevention or treatment of a cholestatic liver disease or increasing bile flow will be an amount sufficient to increase bile flow to the intestine.

The amount of the compound of the invention which is required to achieve the desired biological effect will depend on a number of factors such as the use for which it is intended, the means of administration, and the recipient, and will be ultimately at the discretion of the attendant physician or veterinarian. In general, a typical daily dose for the treatment of a FXR mediated disease and condition, for instance, may be expected to lie in the range of from about 0.01 mg/kg to about 100 mg/kg. This dose may be administered as a single unit dose or as several separate unit doses or as a continuous infusion. Similar dosages would be applicable for the treatment of other diseases, conditions and therapies including the prevention and treatment of cholestatic liver diseases.

Thus, in a further aspect, the present invention provides a pharmaceutical composition comprising, as active ingredient, a compound of the invention together, and/or in admixture, with at least one pharmaceutical carrier or diluent. These pharmaceutical compositions may be used in the prevention or treatment of the foregoing diseases or conditions.

The carrier must be pharmaceutically acceptable and must be compatible with, i.e. not have a deleterious effect upon, the other ingredients in the composition. The carrier may be a solid or liquid and is preferably formulated as a unit dose formulation, for example, a tablet which may contain from 0.05 to 95% by weight of the active ingredient. If desired, other physiologically active ingredients may also be incorporated in the pharmaceutical compositions of the invention.

Possible formulations include those suitable for oral, sublingual, buccal, parenteral (for example subcutaneous, intramuscular, or intravenous), rectal, topical including transdermal, intranasal and inhalation administration. Most suitable means of administration for a particular patient will depend on the nature and severity of the disease or condition being treated or the nature of the therapy being used and on the nature of the active compound, but where possible, oral administration is preferred for the prevention and treatment of FXR mediated diseases and conditions. Formulations suitable for oral administration may be provided as discrete units, such as tablets, capsules, cachets, lozenges, each containing a predetermined amount of the active compound; as powders or granules; as solutions or suspensions in aqueous or non-aqueous liquids; or as oil-in-water or water-in-oil emulsions.

Formulations suitable for sublingual or buccal administration include lozenges comprising the active compound and, typically a flavoured base, such as sugar and acacia or tragacanth and pastilles comprising the active compound in an inert base, such as gelatine and glycerine or sucrose acacia.

Formulations suitable for parenteral administration typically comprise sterile aqueous solutions containing a predetermined concentration of the active compound; the solution is preferably isotonic with the blood of the intended recipient.

Additional formulations suitable for parenteral administration include formulations containing physiologically suitable co-solvents and/or complexing agents such as surfactants and cyclodextrins. Oil-in-water emulsions are also suitable formulations for parenteral formulations. Although such solutions are preferably administered intravenously, they may also be administered by subcutaneous or intramuscular injection.

Formulations suitable for rectal administration are preferably provided as unit-dose suppositories comprising the active ingredient in one or more solid carriers forming the suppository base, for example, cocoa butter.

Formulations suitable for topical or intranasal application include ointments, creams, lotions, pastes, gels, sprays, aerosols and oils. Suitable carriers for such formulations include petroleum jelly, lanolin, polyethyleneglycols, alcohols, and combinations thereof.

Formulations of the invention may be prepared by any suitable method, typically by uniformly and intimately admixing the active compound with liquids or finely divided solid carriers or both, in the required proportions and then, if necessary, shaping the resulting mixture into the desired shape.

For example a tablet may be prepared by compressing an intimate mixture comprising a powder or granules of the active ingredient and one or more optional ingredients, such as a binder, lubricant, inert diluent, or surface active dispersing agent, or by moulding an intimate mixture of powdered active ingredient and inert liquid diluent.

Suitable formulations for administration by inhalation include fine particle dusts or mists which may be generated by means of various types of metered dose pressurised aerosols, nebulisers, or insufflators.

For pulmonary administration via the mouth, the particle size of the powder or droplets is typically in the range 0.5-10 µm, preferably 1-5 µm, to ensure delivery into the bronchial tree. For nasal administration, a particle size in the range 10-500 µm is preferred to ensure retention in the nasal cavity.

Metered dose inhalers are pressurised aerosol dispensers, typically containing a suspension or solution formulation of the active ingredient in a liquefied propellant. During use, these devices discharge the formulation through a valve adapted to deliver a metered volume, typically from 10 to 150 µl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol surfactants, such as oleic acid or sorbitan trioleate, anti-oxidants and suitable flavouring agents.

Nebulisers are commercially available devices that transform solutions or suspensions of the active ingredient into a therapeutic aerosol mist either by means of acceleration of a compressed gas typically air or oxygen, through a narrow venturi orifice, or by means of ultrasonic agitation. Suitable formulations for use in nebulisers consist of the active ingredient in a liquid carrier and comprise up to 40% w/w of the formulation, preferably less than 20% w/w. The carrier is typically water or a dilute aqueous alcoholic solution, preferably made isotonic with body fluids by the addition of, for example, sodium chloride. Optional additives include preservatives if the formulation is not prepared sterile, for example, methyl hydroxy-benzoate, anti-oxidants, flavouring agents, volatile oils, buffering agents and surfactants.

Suitable formulations for administration by insufflation include finely comminuted powders which may be delivered by means of an insufflator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation.

In addition to the ingredients specifically mentioned above, the formulations of the present invention may include other agents known to those skilled in the art of pharmacy, having regard for the type of formulation in issue. For example, formulations suitable for oral administration may include flavouring agents and formulations suitable for intranasal administration may include perfumes.

The following Examples are illustrative and should not be interpreted in any way so as to limit the scope of the invention.

EXAMPLES

In general, the potential of a compound of the invention as a drug candidate can be tested using various assays known in the art. For example, for in vitro validation for FXR: its activity and selectivity can be evaluated using AlphaScreen (biochemical assay); gene expression can be evaluated using RT-PCR (FXR target gene); and cytotoxicity (e.g., HepG2) can be evaluated using ATP content, LDH release, and Caspase-3 activation. For the in vitro validation for TGR5: its activity and selectivity can be evaluated using HTR-FRET (cell-based assay); gene expression can be evaluated using RT-PCR (TGR5 target gene (i.e., cFOS)); and cytotoxicity (e.g., HepG2) can be evaluated using ATP content, LDH release, and Caspase-3 activation. The ADME (absorption, distribution, metabolism, and excretion)/pharmacokinetic properties and in vivo validation of compounds of the invention can also be studied using methods known in the art.

Example 1: Synthesis of Compounds 100 and 101

Compounds 100 and 101 were synthesized according to the scheme below.

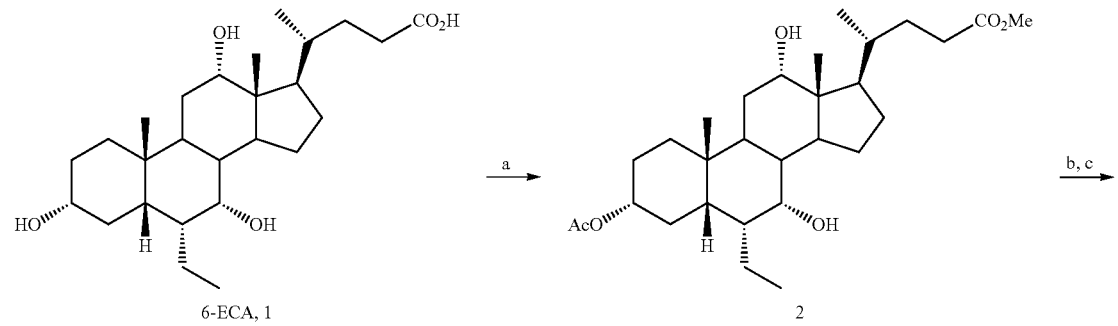

Scheme 1

-continued

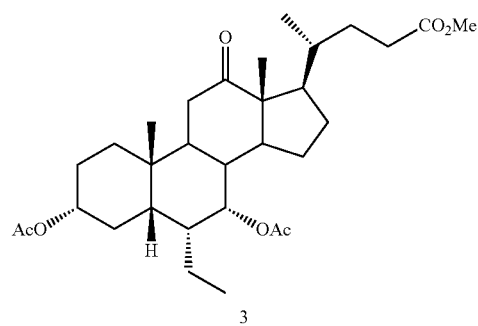
3

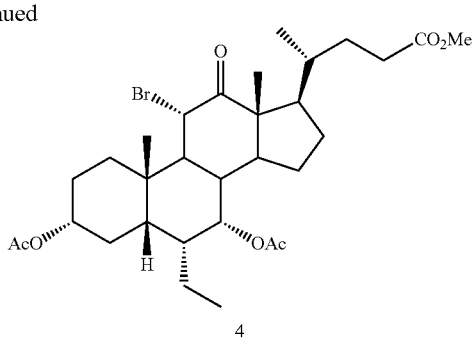
4

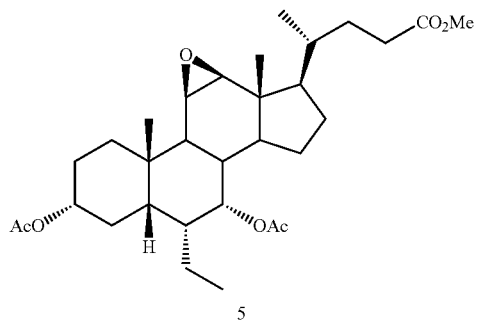
5

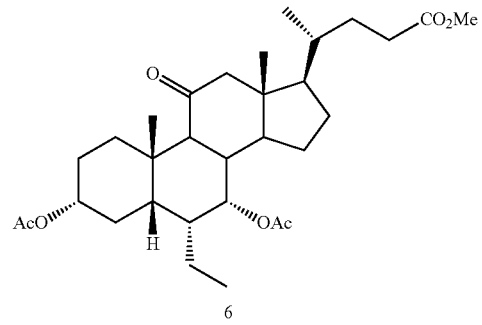
6

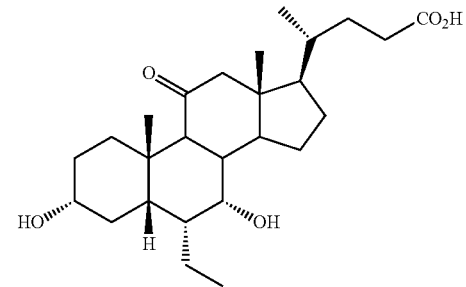
7

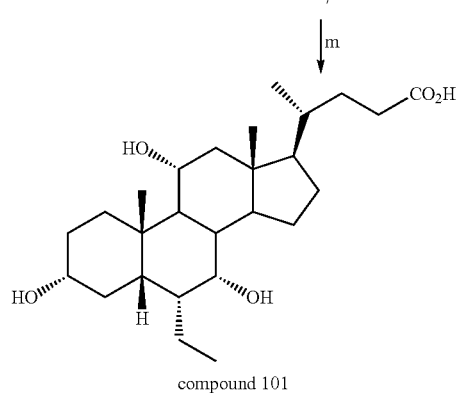
compound 100 compound 101

Reagents and conditions: a) 1) MeOH, p-TSA, ultrasound, 3 h, quantitative; 2) Ac$_2$O, NaHCO$_3$, THF, reflux 12 h, 85%; b) PCC, CH$_2$Cl$_2$, 6 h, 62%; c) Ac$_2$O, Bi(OTf)$_3$, CH$_2$Cl$_2$, 1 h, 91%; d) Br$_2$, Benzene, 30° C. overnight, 74%; e) NaBH$_4$, NaOAc, Pyr, r.t. 2 days, 80%; f) HI 57%, AcOH, r.t. 30 min; g) CrO$_3$, AcOH, r.t. 45 min; h) Zn dust, NaOAc, reflux 20 min; i) NaOH 2M, MeOH, r.t. overnight, 65% from compound 5; l) NaBH$_4$, THF/H$_2$O 4:1, 70%; m) Na(s), sec-BuOH, 50° C., 70%.

The synthesis is based on the use of 6α-ethyl-cholic acid (6-ECA, 1) as starting material which was prepared using methods known in the art. 6-ECA (1) was treated with p-TSA in MeOH under ultrasound irradiation to give the corresponding methyl ester, which was selectively protected at the C3 position by refluxing with Ac$_2$O in the present of NaHCO$_3$ in THF to afford compound 2. Treating compound 2 with PCC in CH$_2$Cl$_2$ at room temperature followed by treatment with Ac$_2$O, Bi(OTf)$_3$ in CH$_2$Cl$_2$ at room temperature afforded the intermediate methyl 3α,7α-diacetoxy-12-oxo-5β-cholan-24-oate (compound 3; about 48% from compound 2).

Treatment of compound 3 with Br$_2$ in benzene for e.g., 12 h yielded compound 4. Reaction of compound 4 with NaBH$_4$ and NaOAc in freshly distilled pyridine gave the corresponding 11β-12β epoxide (compound 5), in about 59% yield after silica gel purification. The reaction of compound 5 with HI in AcOH at room temperature afforded the halohydrine intermediate which were then oxidized at C11 position with $CrO_3$ in AcOH to generate compound 6. Reaction of compound 6 with Zn dust in boiling AcOH and alkali hydrolysis (NaOH/MeOH) afforded 3α,7α-hydroxy-12-keto-5b-cholan-24-oic acid (compound 7; about 65% yield from compound 5).

Compound 7 was stereoselectively reduced at the C11-carbonyl using $NaBH_4$ in a mixture of $THF/H_2O$ (4:1, v/v) to give 3α,7α,11β-trihydroxy-6α-ethyl-5β-cholan-24-oic acid (Compound 100; about 27% from compound 3), after chromatographic purification to afford Compound 100. Alternatively, compound 7 was reduced with sodium in sec-BuOH at 50° C. to give Compound 101 (about 70% yield), after purification.

Example 2: Compound 100 is a Potent, Specific FXR Agonist

In the nucleus, ligand-bound nuclear receptors (NRs) modulate initiation of transcription by directly interacting with the basal transcriptional machinery or by contacting bridging factors called coactivators (Onate S A, et al., Science 1995; 270:1354-1357; Wang J C, et al., J Biol Chem 1998; 273:30847-30850; Zhu Y, et al., Gene Expr 1996; 6:185-195). The ligand-dependent interaction of NRs with their coactivators occurs between activation function 2 (AF-2), located in the receptor ligand-binding domain (LBD) and the nuclear receptor boxes (NR box) located on the coactivators (Nolte R T, et al., Nature 1998; 395:137-143). Several lines of evidence have demonstrated that the LXXLL peptide sequence present in the NR box represents a signature motif that facilitates the interaction of different proteins with the AF-2 region (Heery D M, et al., Nature 1997; 387:733-736; Torchia J, et al., Nature 1997; 387:677-684).

AlphaScreen was used with the aim of identify novel modulators by taking advantage of the bimolecular interaction prevailing between FXR and the LXXLL motif present in the NR box of the steroid receptor coactivator 1 (SRC-1).

Human FXR-LBD-GST was incubated with increasing concentrations of the indicated ligands in the presence of biotinylated LXXLL SRC-1 peptide. The AlphaScreen signal increases when the complex receptor-coactivator is formed. $EC_{50}$ values were 8.9 µM for chenodeoxycholic acid (CDCA; which is a positive control), 0.16 µM for Compound A, and 0.16 µM for Compound 100. These results are the mean±S.D. of triplicate samples from a representative experiment of three performed. The AlphaScreen assay is a very robust and reproducible assay, as shown by the Z' factor of 0.84 (Zhang J H, et al., J Biomol Screen 1999; 4:67-73). Thus, Compound 100 is a highly potent FXR agonist.

Further, the data in the table below show that Compound 100 is selective for human FXR and is not active for human TGR5.

TABLE 1

| Compound | AlphaScreen Assay Human FXR Ref. CDCA = 15 ± 3 µM | HTR-FRET (cAMP) Human TGR5 (NCI-H716 cells) Ref. LCA = 7 ± 3 µM | HTR-FRET (cAMP) Human TGR5 overexpression Ref. LCA = 0.9 ± 0.1 µM |
|---|---|---|---|
| Compound 100 | 0.180 ± 0.02 | No activity | No activity |
| Compound 101 | 3 ± 2 | 41.5 | |
| Compound A | 0.2 ± 0.018 | 15 ± 5 | |
| Compound B | 0.03 | 0.63 | |
| Compound C | 175 | 0.9 | |

Additionally, using the AlphaScreen assay, it was demonstrated that Compound 100 specifically activates FXR and does not activate 13 other nuclear receptors involved in the metabolic pathways.

TABLE 2

| Compound | FXR Activation (CDCA = 10-20 µM) $EC_{50}$ (µM) | LXRβ Activation (T0901317 = 0.08 µM) $EC_{50}$ (µM) | PXR Activation (SR-12183 = 0.062 µM) $EC_{50}$ (µM) | CAR Activation (CITCO = 0.005 µM) $EC_{50}$ (µM) | PPARα Activation (GW7647 = 0.003 µM) $EC_{50}$ (µM) | PPARδ Activation (GW0742 = 0.004 µM) $EC_{50}$ (µM) | PPARγ Activation (GW1929 = 0.012 µM) $EC_{50}$ (µM) |
|---|---|---|---|---|---|---|---|
| (Reference standard) | | | | | | | |
| Compound A | 0.16 | No activity | No activity | No activity | No activity | No activity | No activity |
| Compound B | 0.03 | No activity | No activity | 44* | No activity | No activity | No activity |
| Compound 100 | 0.16 | No activity | No activity | No activity | No activity | No activity | No activity |

| Compound | RARα Activation (ATRA = 0.001 µM) $EC_{50}$ (µM) | VDR Activation (DiHydroxyVitD3 = 0.005 µM) $EC_{50}$ (µM) | TR Activation (T3 = 0.0001 µM) $EC_{50}$ (µM) | PR Activation (Corticosterone = 0.050 µM) $EC_{50}$ (µM) | RXR Activation (9cisRA = 0.004 µM) $EC_{50}$ (µM) | GR Activation (Budenoside = 0.0002 µM) $EC_{50}$ (µM) | ER Activation (Estradiol = 0.001 µM) $EC_{50}$ (µM) |
|---|---|---|---|---|---|---|---|
| (Reference standard) | | | | | | | |
| Compound A | No activity | No activity | No activity | No activity | No activity | No activity | No activity |
| Compound B | No activity | No activity | No activity | No activity | No activity | No activity | No activity |
| Compound 100 | No activity | No activity | No activity | No activity | No activity | No activity | No activity |

*inverse agonist.

Values for compound B taken from Rizzo G., et al., *Mol. Pharm.*, 2010; 78: 617-630.

FXR activation by Compound 100 was also tested in cell-based transactivation assays with the use of HEK293T cell line transiently transfected with Gal4-FXR-LBD chimera and the (UAS)5-Luc system (FIG. 1). FXR activation by Compound 100 was comparable to that induced by compound A indicating that these compounds are potent FXR agonists in cell-based assays. FIG. 1 is a graph showing the activity of Compound 100 in comparison to compound A in a transactivation assay in HEK293T cells. NT is FXR vector-transfected cells without exposure to compound A or Compound 100. Values are represented in M.

Bile acids (BAs) modulate not only several nuclear hormone receptors, but are also agonists for the G protein-coupled receptor (GPCR) TGR5 (Makishima M, et al., *Science* 1999; 284:1362-1365; Parks D J, et al., *Science* 1999; 284:1365-1368; Maruyama T, et al., *Biochem Biophys Res Commun* 2002; 298:714-719; Kawamata Y, et al., *J Biol Chem* 2003; 278:9435-9440). Signalling via FXR and TGR5 modulates several metabolic pathways, regulating not only BA synthesis and enterohepatic recirculation, but also triglyceride, cholesterol, glucose, and energy homeostasis. To evaluate the capacity of a compound of the invention to activate TGR5, Compound 100 and other comparison compounds were screened for an increase of intracellular cAMP as a read-out for TGR5 activation. Human enteroendocrine NCI-H716 cells constitutively expressing TGR5 were exposed to increasing concentrations of Compound 100, and intracellular cAMP levels were measured by TR-FRET. Lithocholic acid (LCA) was used as positive control.

Figure 2:
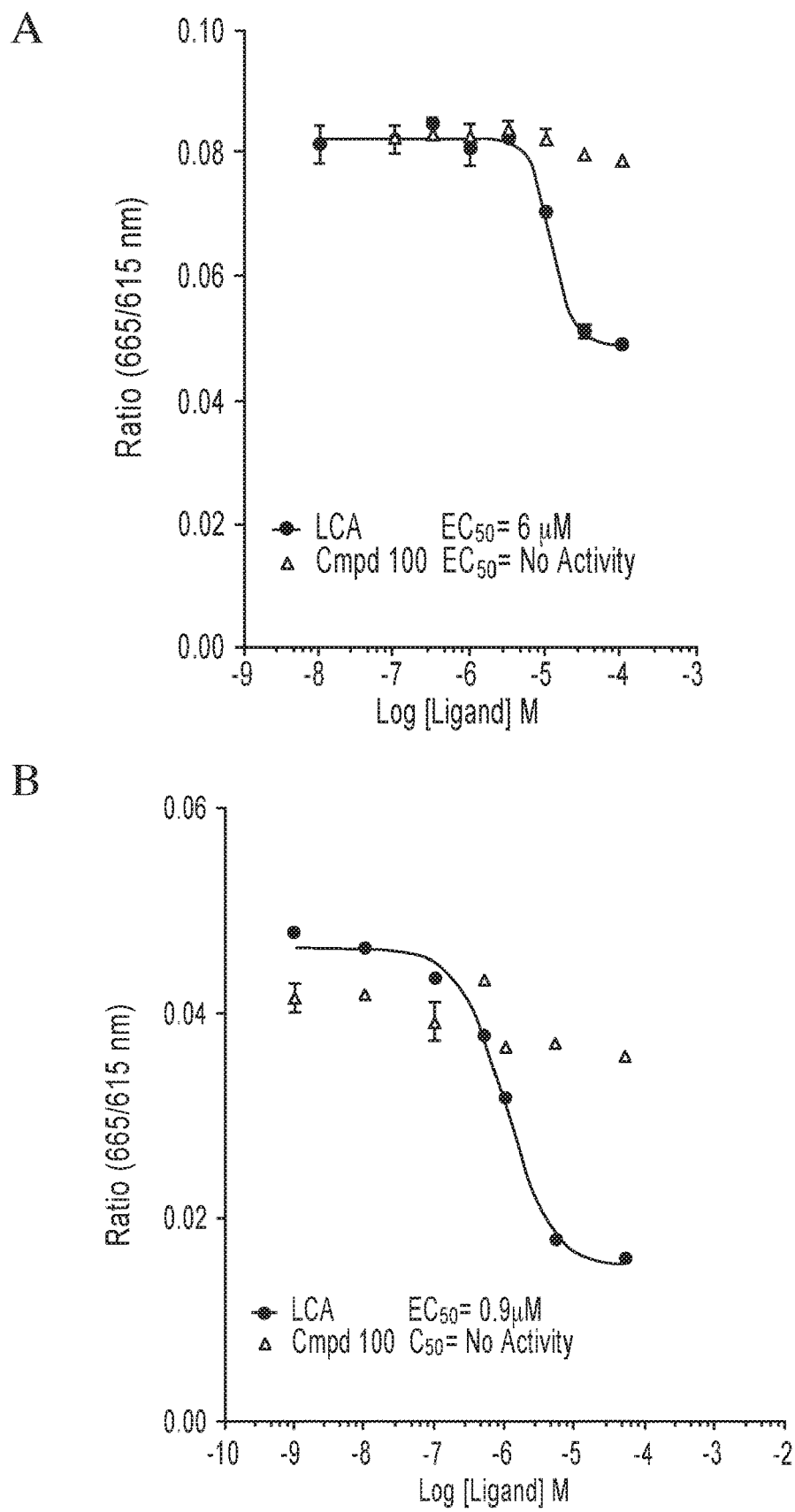
FIG. 2 is a series of graphs showing the lack of TGR5 activity of a compound of the invention in human enteroendocrine cells expressing TGR5 at physiological level (A) and in human Chinese hamster ovary (CHO) cells overexpressing TGR5 (B).

As shown in FIG. 2A, Compound 100 does not induce TGR5 activity in cells expressing the receptor physiologically as no change in the level of intracellular cAMP was observed. To further assess if Compound 100 could bind TGR5, a clonal cell line over-expressing TGR5 was exposed to different concentrations of Compound 100. The results illustrated in FIG. 2B show that even with the over-expression of the TGR5 receptor, Compound 100 had no relevant effect. FIG. 2A is a graph showing the TGR5 activity of Compound 100 (no activity) and LCA in human enteroendocrine cells expressing TGR5 at physiological level. Results are shown as the mean+S. D. of triplicate samples from a representative experiment of three performed. FIG. 2B is a graph showing the TGR5 activity of Compound 100 (no activity) and LCA in human Chinese hamster ovary (CHO) cells over-expressing TGR5.

Example 3: FXR Target Genes Modulated by Compound 100

To evaluate the capacity of Compound 100 to modulate FXR target genes, quantitative RT-PCR assays were performed. HepG2 cells were selected as a relevant cell line to determine whether a compound of the invention can regulate the endogenous FXR genetic network. The ability of a compound of the invention to induce FXR target genes was assessed by isolating total RNA from cells treated overnight with 1 µM of compounds A, B, and 100. Compound A is established as a potent FXR selective agonist and compound B is established as a dual potent FXR/TGR5 agonist. Compound 100's gene activation profile in HepG2 cells was compared to the profiles of compounds A and B. (Pellicciari, R, et al., J Med Chem. 2002; August 15; 45: 3569-72; Rizzo, G, et al., *Mol. Pharm.*, 2010; 78: 617-630).

FXR regulates the expression of several target genes involved in BA homeostasis. Briefly, FXR plays a central role in several metabolic pathways, including i.e., lipid metabolism, bile-acids metabolism, and carbohydrate metabolism. Regarding gene expression profiling, the genes encoding proteins involved in lipid metabolism include, e.g., APOCII, APOE, APOAI, SREBP-1C, VLDL-R, PLTP, and LPL; the genes encoding proteins involved in bile-acids metabolism include, e.g., OSTα/β, BSEP, MRP2, SHP, CYP7A1, FGF19, SULT2A1, and UGT2B4; and the genes encoding proteins involved in carbohydrate metabolism include, e.g., PGC1a, PEPCK, and GLUT2.

As shown in FIGS. 3A-3H, Compound 100 activation of FXR indirectly represses the expression of the BA biosynthetic enzymes CYP7A1 by increasing the levels of the nuclear receptor SHP in the liver and intestine and increasing the level of FGF19 (Goodwin, B, et al., *Mol. Cell* 2000; 6: 517-526). Compound 100 activated FXR also positively regulates the expression of genes encoding proteins involved in the transport of BA, including, BSEP, and OSTα and OSTβ. Newly synthesized BAs are conjugated with taurine or glycine and then actively secreted in the gall bladder, FXR regulates both of these critical processes. Monoanionic- and dianionic-conjugated BAs are then actively secreted in the gall bladder by BSEP and the multidrug related protein 2 (MRP2), respectively. These transporters belonging to the ABC transporter family and are both induced by FXR at the transcriptional level. The regulation of these ABC transporters is of critical importance in order to avoid BA accumulation in the liver and consequent hepatic injury (Schinkel A H, et al., Mammalian drug efflux transporters of the ATP binding cassette (ABC) family: an overview. *Adv Drug Deliv Rev.* 2012; September 13).

Figure 3:
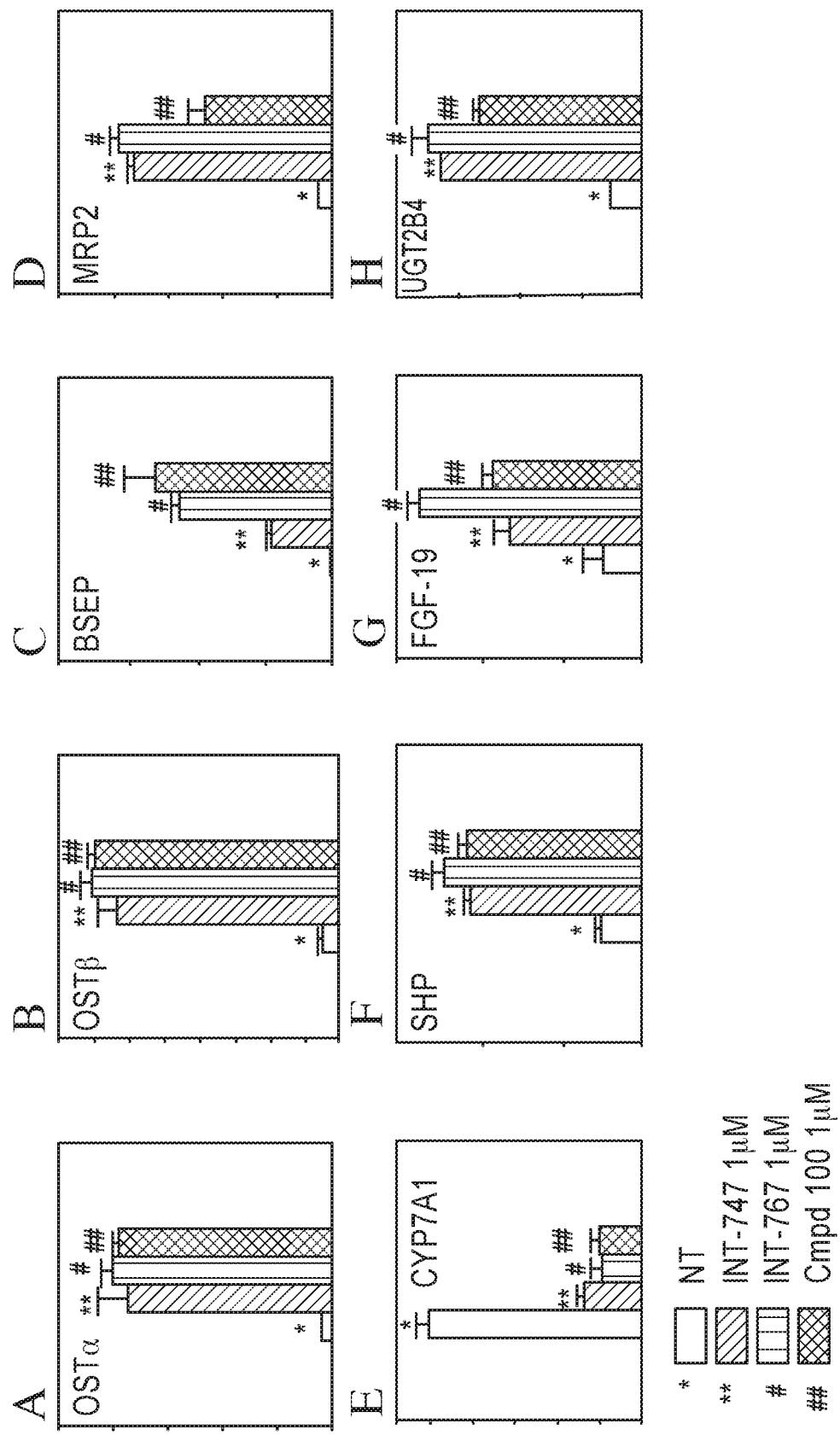
FIG. 3 is a series of graphs showing the activity of a compound of the invention and other comparison compounds in regulating expression of OSTα (A), OSTβ (B), BSEP (C), MRP2 (D), CYP7A1 (E), SHP (F), FGF-19 (G), and UGT2B4 (H).

FIG. 3 are a series of graphs showing the activity of Compound 100 and other comparison compounds in regulating expression of OSTα (A), OSTβ (B), BSEP (C), MRP2 (D), CYP7A1 (E), SHP (F), FGF-19 (G), and UGT2B4 (H). Note in the FIGS. 3A-3H, the y-axis displays folds change in expression relative to untreated cells. The data were normalized relative to B2M. The error bars display the standard error of the three replicates.

FXR activation contributes to reverse cholesterol transport, a process that results in the delivery of cholesterol from peripheral tissues to the liver for biliary disposal and consequent fecal elimination (Lambert, G, et al., *J Biol Chem* 2003; 278, 2563-70). In this metabolic scenario, FXR regulates the expression of phospholipids transfer protein (PLTP), responsible for the transfer of phospholipids and cholesterol from LDL to HDL, hepatic lipoproteins, such as ApoE, ApoC-I, ApoC-IV, and scavenger receptor B1(SRB1), which is involved in the hepatic uptake of HDL.

FXR controls triglyceride (TG) metabolism by regulating hepatic de novo lipogenesis and triglyceride clearance. Upon activation by Compound 100, FXR down regulates the expression of SREBP-1c, a transcription factor that plays a critical role in stimulating fatty acid synthesis and lipogenesis (FIGS. 4A-4D) (Landrier, J F, et al., *J Clin Invest* 2004; 113, 1408-18). In addition to the reduction of de novo lipogenesis, FXR activation also modulates TG clearance. This additional TG-lowering effect of FXR is explained at the molecular level by the induction of key genes, such as Apo-C-I1 LPL and VDL receptor (Kast, H R, et al., *Mol Endocrinol* 2001; 15, 1720-8).

FIG. 4 are a series of graphs showing the activity of Compound 100 and other comparison compounds in regulating PLTP involved in lipid metabolism (A), SREBP-1C (B), APOCII (C), and PPARγ (D). Note in the FIGS. 4A-4D, the y-axis displays folds change in expression relative to not treated cells. The data were normalized relative to B2M. The error bars display the standard error of the three replicates.

Figure 5:
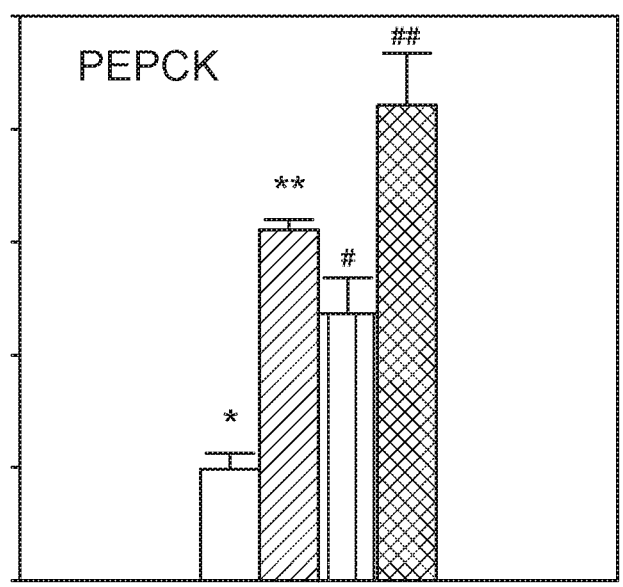
FIG. 5 is a graph showing the regulation of a compound of the invention and other comparison compounds on PEPCK gene.

FXR may also have a role in carbohydrate metabolism. (Ma K, et al., *J Clin Invest.* 2006; 116:1102-9). PEPCK gene regulation was studied (FIG. 5) using Compound 100. FIG. 5 is a graph showing the regulation of Compound 100 and other comparison compounds on PEPCK gene. The y-axis displays folds change in expression relative to not treated cells. The data were normalized relative to B2M. The error bars display the standard error of the three replicates.

Collectively the gene expression studies showed that Compound 100 modulates the same FXR target genes as compound A or B (also see Table 3).

TABLE 3

| gene | Compound A (1 μM) | Compound B (1 μM) | Compound 100 (1 μM) |
|---|---|---|---|
| OSTα | up | up | up |
| OSTβ | up | up | up |
| BSEP | up | up | up |
| SHP | up | up | up |
| CYP7α1 | down | down | down |
| UGT2B4 | up | up | up |
| MRP2 | up | up | up |
| FGF-19 | up | up | up |
| PPARγ | up | up | up |
| PLTP | up | up | up |
| APOCII | up | up | up |
| PEPCK | up | up | up |
| SREBP-1C | down | down | down |

Example 4: Compound 100 does not Exert Cytotoxic Effects in HepG2 Cells

To evaluate in vitro cytotoxicity of Compound 100, two different assay methods were employed. The assays evaluated cell viability by measuring ATP levels and cytotoxicity by measuring LDH release. Adenosine Triphosphate (ATP) nucleotide represents the source of energy at the basic molecular level, as it is a multifunctional molecule that is used in every cell as a coenzyme and is an integral part of the mitochondrial DNA (Kangas L, et al., Medical Biology, 1984; 62, 338-343; Crouch S P M, et al., *J. mmunol. Methods,* 1993; 160, 81-88; Petty R D, et al., *J. Biolumin. Chemilumin.* 1995; 10, 29-34). It has been called the "molecular unit of currency" when it comes to intracellular energy transfer. This is to ensure the important role of ATP in metabolism and a drop in ATP content is the first step in revealing cellular damage (Storer R D, et al., *Mutation Research,* 1996; 368, 59-101; Cree I A, Andreotti P E., *Toxicology in Vitro,* 1997; 11, 553-556).

Cell viability was determined as measure of intracellular ATP related to the time of exposure and concentration of the test compounds (Sussman, N L.; *Promega Cell Notes,* Issue 3. 2002).

Figure 6:
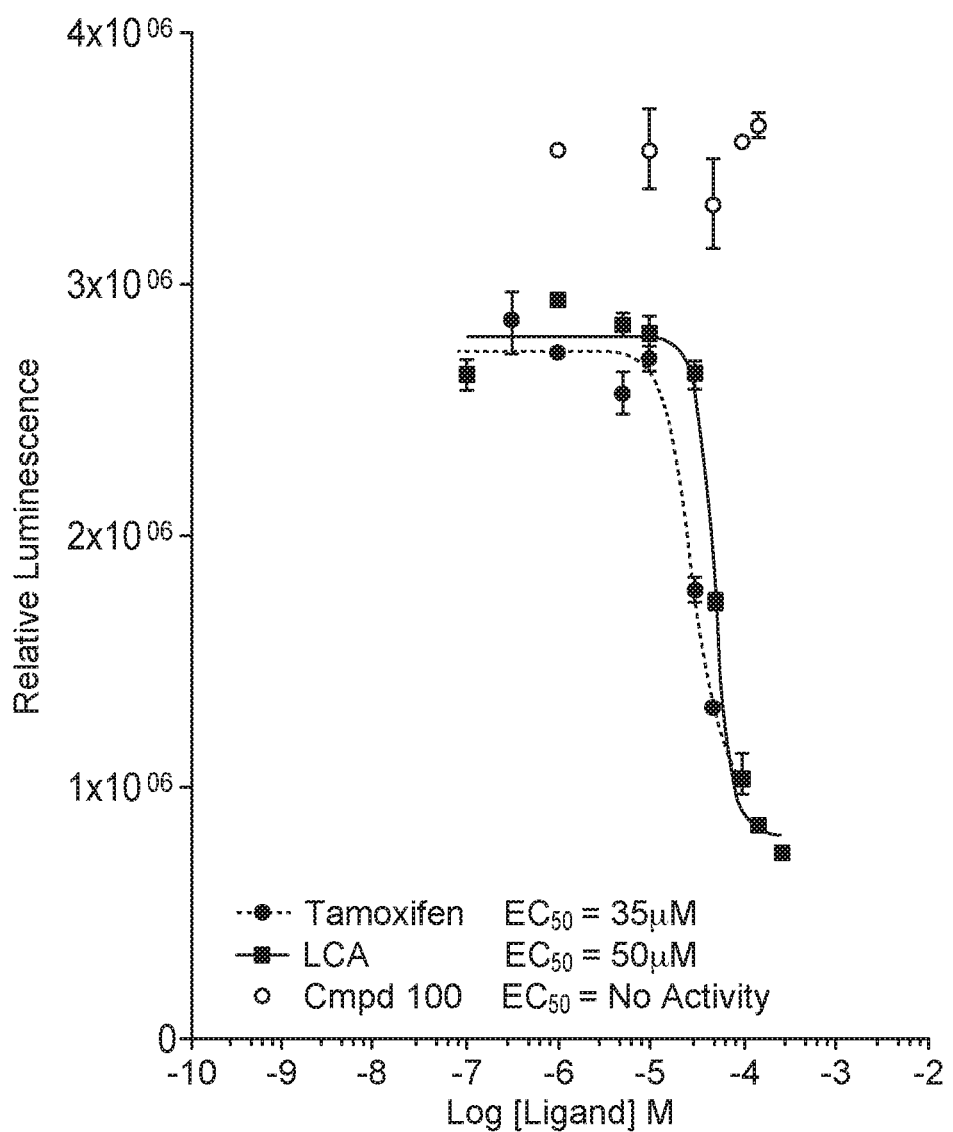
FIG. 6 is a graph showing the measurement of ATP in HepG2 cells, treated with the indicated concentrations of a compound of the invention for 4 h.

FIG. 6 is a graph showing the measurement of ATP in HepG2 cells, treated with the indicated concentrations of compounds for 4 h. It demonstrated that all cells in presence of different concentrations of Compound 100 were viable as cells treated with the vehicle alone, i.e., all cells treated with Compound 100 remain viable (100%). LCA, a well-known cytotoxic bile acid, was used as comparator and Tamoxifen was used as positive controls for the assays.

An additional method to determine the viability of cells is to detect the integrity of the membrane that defines the cellular compartmentalization. Measuring the leakage of components out of the cytoplasm, in damaged cell membranes, indicates loss of membrane integrity, and LDH release is the method used to determine common toxicity in cells. HepG2 cells were treated with Compound 100, serial dilutions were performed, LCA dilutions were added to the plated cells as assay control together with no-cell and untreated cells. The assay was performed in triplicate for each test compound concentration.

The results show that Compound 100 does not induce any cytotoxic effect on HepG2 cells. Lithocolic Acid increased LDH release at 70 μM whilst the control Tamoxifen exerted the cytotoxic effects at approximately 25 μM (see Table 4).

TABLE 4

| Compound | Membrane integrity $EC_{50}$ (μM) (LDH measure) |
|---|---|
| Tamoxifen | 35 ± 10 |
| LCA | 75 ± 5 |
| Compound A | 190 ± 30 |
| Compound B* | 670 |
| Compound 100 | No toxicity (100% living cells) |
| Compound 101 | No toxicity (100% living cells) |

*Rizzo et al., Mol. Pharm. 2010

Example 5: Compound 100 does not Inhibit Cytochrome P450 Enzymes

To evaluate the potential of Compound 100 for drug-drug interactions, the six main CYP450 isoforms (CYP1A2, CYP2C9, CYP2C19, CYP2D6, CYP2E1, CYP3A4) were investigated. (Obach, R S, et al., *J Pharmcol Exp Ther,* 2006; 316(1): p. 336-48).

To determine interaction between Compound 100 and cytochrome P450 enzymes, Compound 100 was analyzed by its capacity to inhibit (or not) the production of a fluorescent signal, using recombinant CYP450 proteins (baculosomes; Invitrogen), substrates and inhibitors (Bidstrup, T B, et al., Br J Clin Pharmacol, 2003; 56(3): p. 305-14). As a positive control, a selective inhibitor for each CYP450 isoform was tested in the same plate (Table 5).

TABLE 5

| CPY450 | Compound A $IC_{50}$ (μM) | Compound B $IC_{50}$ (μM) | Compound 100 $IC_{50}$ (μM) |
|---|---|---|---|
| CYP1A2 Reference: Furafylline = 0.5 μM | >10 | >10 | >10 |
| CYP3A4 (Green Substrate) Reference: Ketoconazole = 0.044 μM | >10 | >10 | >10 |
| CYP3A4 (Blue Substrate) Reference: Ketoconazole = 0.04 μM | >10 | >10 | >10 |
| CYP2C9 Reference: Sulfaphenazole = 0.4 μM | >10 | >10 | >10 |
| CYP2C19 Reference: Miconazole = 0.06 μM | >10 | >10 | >10 |
| CYP2D6 Reference: Quinidine = 0.01 μM | >10 | >10 | >10 |
| CYP2E1 Reference: DCC = 0.4 μM | >10 | >10 | >10 |

IC$_{50}$>10 µM means that the compound does not inhibit the CYP450. The results obtained demonstrated that Compound 100, like compounds A and B, does not inhibit the Cytochrome P450 enzymes tested, showing that Compound 100 is not likely to be influenced by drug-drug interaction effects. (Rizzo, G, et al., *Mol Pharm,* 2010; 78: 617-630).

Example 6: Compound 100 does not Inhibit Human ERG Potassium Channel

To determine ion channel function, PREDICTOR™ hERG Fluorescence Polarization assay was employed as it provides an efficient method for an initial determination of the propensity of test compounds to block the hERG channel (Dorn, A, et al. *J Biomol Screen,* 2005; 10(4): 339-47). The assay is based on the assumption that the hERG potassium channel activity contributes to the resting membrane potential in permanently transfected cells, and thus a block of hERG channels should result in a depolarization of the cell membrane. The assay was designed to identify potential hERG channel blockers by producing data that accurately correlates with patch-clamp electrophysiology studies. Results from the PREDICTOR™ assay demonstrate a high correlation with those obtained from patch clamp techniques (Table 6) (Dorn, A, et al. *J Biomol Screen,* 2005; 10(4): 339-47).

TABLE 6

| Compound | Patch-Clamp* | Radioligand* IC$_{50}$ (nM) | FP |
|---|---|---|---|
| Astemizole | 1.2 | 1 | 1.3 |
| Dofetilide | 12 | 40 | 6.9 |
| Terfenadine | 16 | 30 | 23 |
| E-4031 | 48 | 20 | 34 |
| Bepridil | 550 | 170 | 210 |
| Thioridazine | 1250 | 510 | 708 |
| Fluoxetine | 990 | 2230 | 4310 |
| Amitripyline | 10000 | f2440 | 11200 |

Table 6 show the comparison of IC$_{50}$ values generated with the PREDICTOR™ hERG Fluorescence Polarization assay with reported IC so values from patch-clamp and radioligand displacement assays.

Membrane preparations from Chinese hamster ovary cells stably transfected with hERG potassium channel were used to evaluate the potential inhibitory effect of Compound 100 on this channel using the PREDICTOR™ fluorescence polarization assay. Reduction of membrane polarization as a result of inhibition of the hERG potassium channel is directly correlated with a reduction of the fluorescence polarization (FP). The results show that like compounds A and B, Compound 100 does not block or inhibit the hERG potassium channel.

The assay was performed in triplicate by using a 16-point dose-response of test compound and the positive controls E-4031 and Tamoxifen. An IC$_{50}$ of 15 nM (ΔmP=163) for E-4031 and 1.4 µM (ΔmP=183) for Tamoxifen were obtained. The assay window more than 100 mP (millipolarization) is considered good. Z' value was 0.78 indicates an excellent assay. The non-linear regression curves were obtained by GraphPad Prism (GraphPad Software Inc.) analysis, to calculate the IC$_{50}$ values.

Briefly, signalling through FXR modulates a variety of metabolic pathways, so selective FXR modulators are attractive candidates for the treatment of a range of chronic diseases affecting liver, kidney, as well as metabolic diseases. Results in the examples described herein characterize Compound 100, as a potent and specific FXR agonist.

Remarkably, although it potently activated FXR, Compound 100 showed no activity against other nuclear receptors and did not active the bile acid GPCR TGR5. In addition to high nuclear receptor selectivity, Compound 100 possesses a pharmacological profile suitable for a drug candidate. Compound 100 shows no cytotoxic effect on human HepG2 liver cells, indicating a lack of liver toxicity, and does not inhibit any of the CYP450 enzymes tested, indicating that Compound 100 is devoid of significant drug-drug interaction risk. Further, Compound 100 does not inhibit the human ERG potassium channel.

The combined selectivity and potency of Compound 100 together with its favorable drug-like properties, in particular an excellent safety profile, make Compound 100 an attractive candidate for treating and preventing disease.

Example 7: Physiochemical Properties of Compound 100

Physiochemical properties of Compound 100 such as water solubility, critical micellular concentration, surface tension and Log PA were determined using methods known in the art. These properties of Compound 100 were compared with natural and synthetic analogues (Table 7).

TABLE 7

| Bile Acid | Ws[a] (µM) | CMC[b] (mM) | ST$_{CMC}$[c] (Dyne/cm) | LogP$_{A-}$[d] |
|---|---|---|---|---|
| Compound 100 | 143-150 | 15.8 | 47.8 | 0.8 |
| CA | 273 | 9-11 | 49.0 | 1.1 |
| CDCA | 32 | 3.2 | 45.5 | 2.2 |
| UDCA | 7-7.5 | 6-10 | 50.5 | 2.2 |
| TCDCA | hs | 3.0 | — | 0.9 |
| TUDCA | hs | 2.2 | — | 1.1 |
| Compound A | 9 | 2.9 | 43.2-48.8 | 2.5 |
| Compound B | hs | 1.3 | 43.3-47.9 | 2.0 |
| Compound C | 99 | 2 | 50.1 | 1.4 |
| Compound D | 15 | — | — | 2.9 |
| Compound E | 120 | 5.9 | 52.4 | 1.6 |

Figure 7:
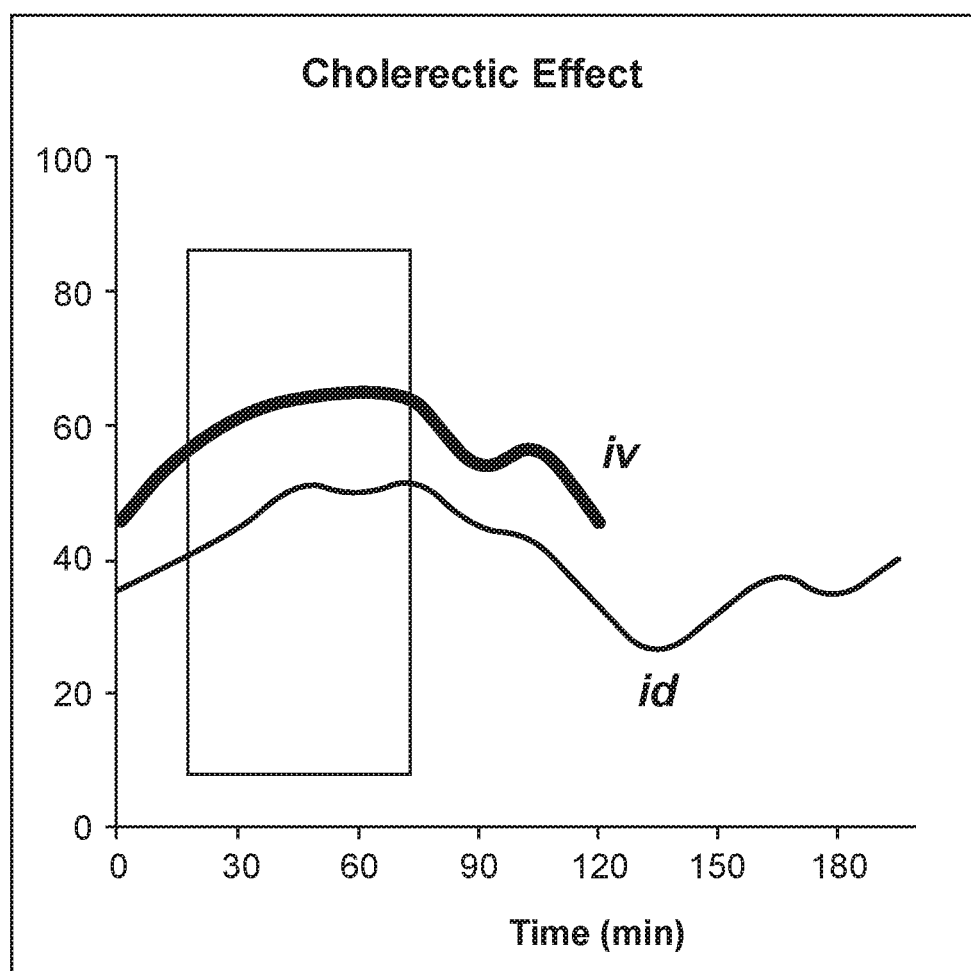
FIG. 7 is a series of graphs showing the choleretic effect of Compound 100 for id and iv administration (A), the secretion of Compound 100 over time for id and iv administration (B), and the plasma concentration of Compound 100 over time (C).
Figure 7:
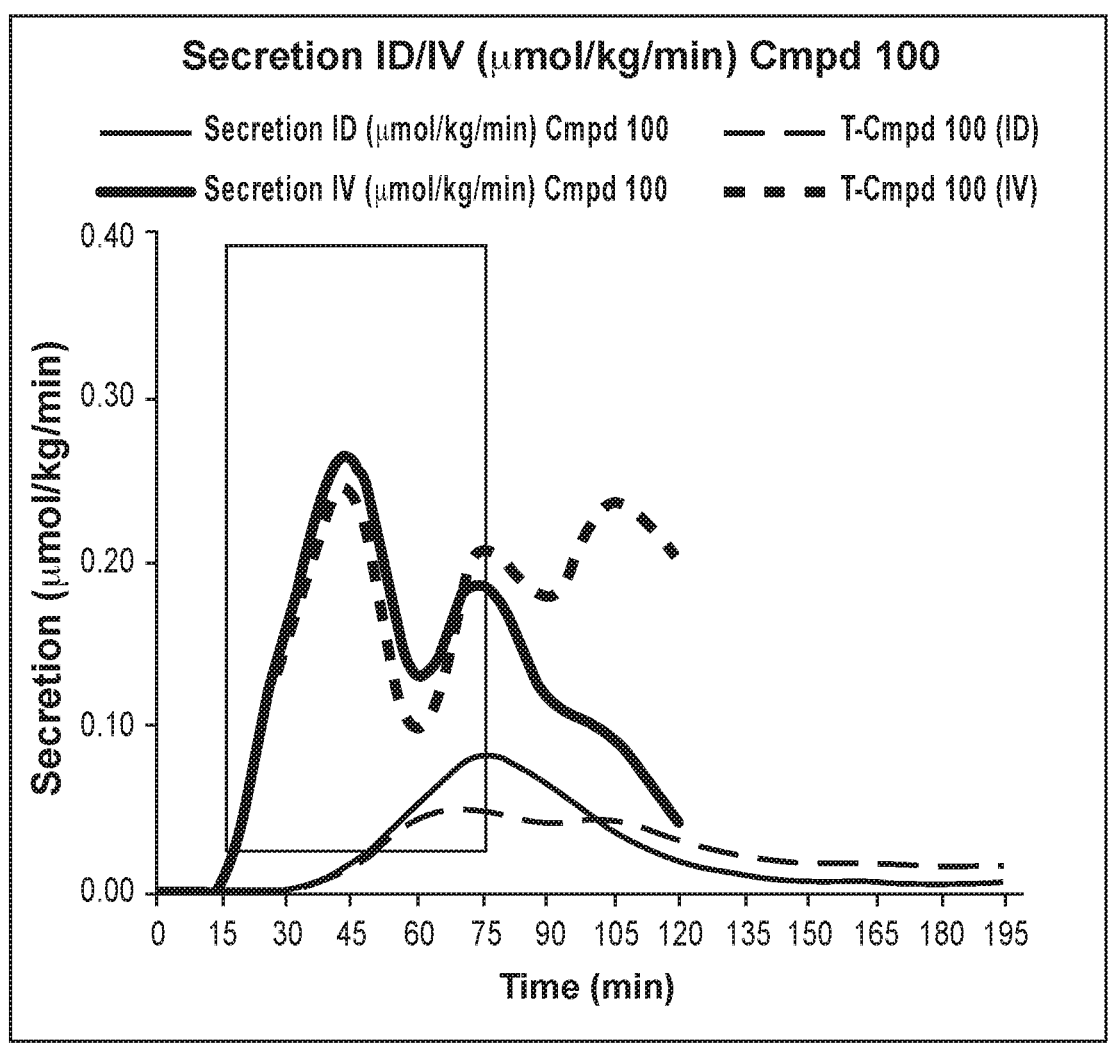
Figure 7:
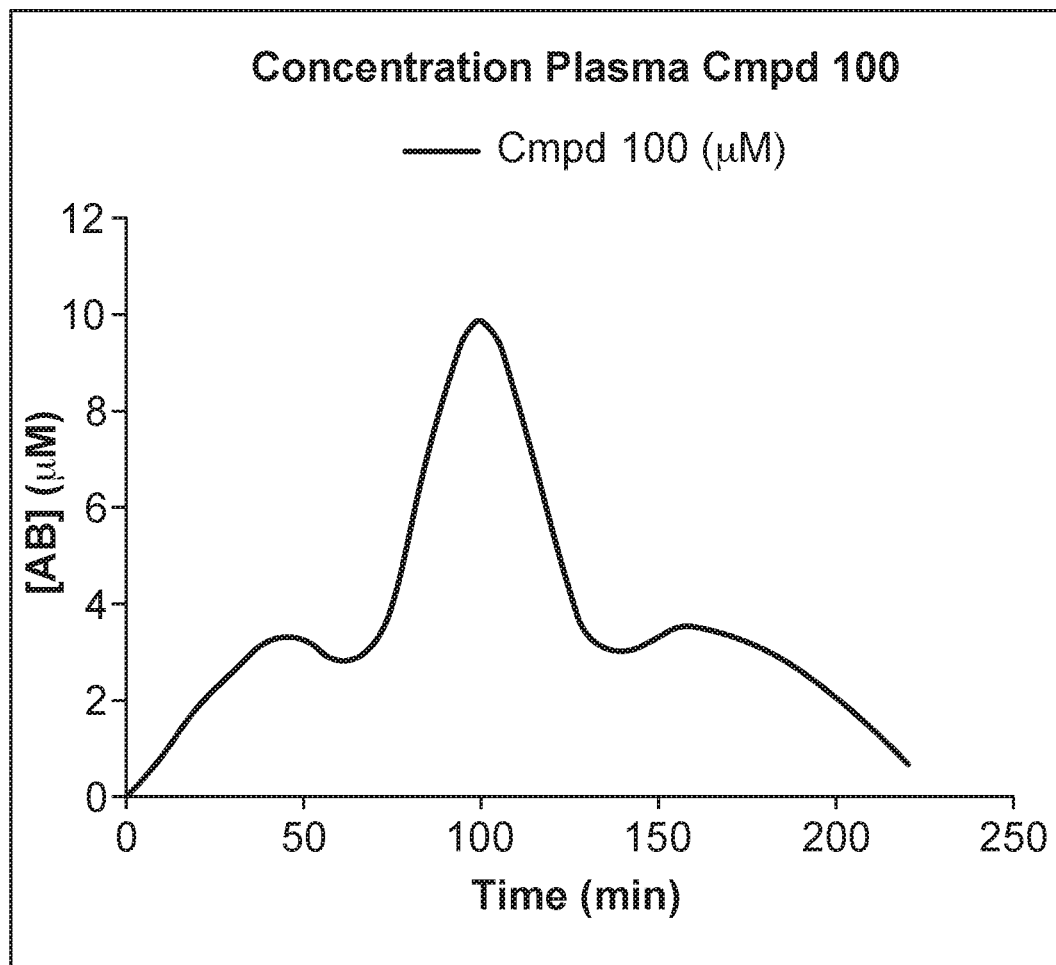

[a]Ws: water solubility refers to BA as protonated species and therefore not evaluated for Compound B, TCDCA and TUDCA which are highly soluble (hs);
[b]CMC: Critical Micellar Concentration determined in 0.15M NaCl water solution;
[c]ST$_{cmc}$: Surface Tension at CMC in 0.15M NaCl water solution;
[d]LogP$_{A-}$: 1-octanol-water partition coefficient of the studied bile acids as ionized species;

Example 8: Pharmacokinetics and Metabolism in Bile Fistula Rat after Id and Iv Administration; In-Vivo The in-vivo models, rats, were administered single dose of Compound 100 at 1 µmol/min/Kg.1 hour (see FIGS. 7A, 7B, and 7C). FIG. 7A is a graph showing the choleretic effect of Compound 100 for id and iv administration. FIG. 7B is a graph showing the secretion of Compound 100 over time for id and iv administration. FIG. 7C is a graph showing the plasma concentration of Compound 100 over time.

EQUIVALENTS

Those skilled in the art will recognize, or be able to ascertain using no more than routine experimentation, many equivalents to the specific embodiments and methods described herein. Such equivalents are intended to be encompassed by the scope of the present invention.

All patents, patent applications, and literature references cited herein are hereby expressly incorporated by reference.

The invention claimed is:

1. A method of treating a chronic liver disease or condition in a subject, comprising administering to the subject in need thereof an effective amount of a compound of formula I:

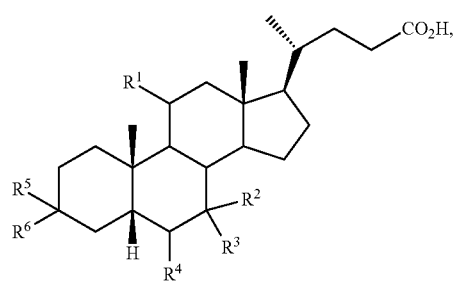
(I)

or a pharmaceutically acceptable salt or amino acid conjugate thereof, wherein:

- $R^1$ is hydroxyl;
- $R^2$ is hydrogen, hydroxyl, alkyl, or halogen, wherein said alkyl is unsubstituted or substituted with one or more $R^a$;
- $R^3$ is hydrogen, hydroxyl, alkyl, or halogen, wherein said alkyl is unsubstituted or substituted with one or more $R^b$;
- $R^4$ is hydrogen, alkyl, alkenyl, alkynyl, or halogen, wherein said alkyl is unsubstituted or substituted with one or more $R^c$;
- $R^a$, $R^b$, and $R^c$ are each independently halogen or hydroxyl;
- $R^5$ is hydroxyl, $OSO_3H$, $OSO_3^-$, $OCOCH_3$, $OPO_3H$, $OPO_3^{2-}$, or hydrogen; and
- $R^6$ is hydroxyl, $OSO_3H$, $OSO_3^-$, $OCOCH_3$, $OPO_3H$, $OPO_3^{2-}$, or hydrogen;
- or taken together $R^5$ and $R^6$ with the carbon atom to which they are attached form a carbonyl, wherein the chronic liver disease or condition is nonalcoholic steatohepatitis (NASH).

2. The method of claim 1, wherein the compound of formula I is

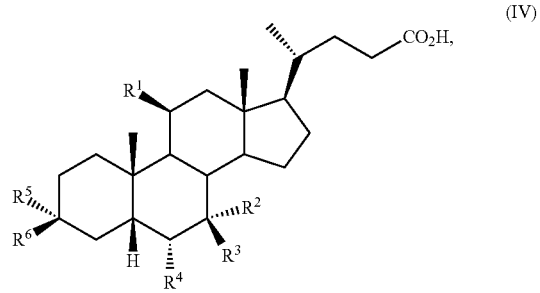
(IV)

or a pharmaceutically acceptable salt or amino acid conjugate thereof.

3. The method of claim 1, wherein $R^4$ is alkyl.

4. The method of claim 3, wherein $R^4$ is ethyl.

5. The method of claim 1, wherein the compound of formula I is compound 100

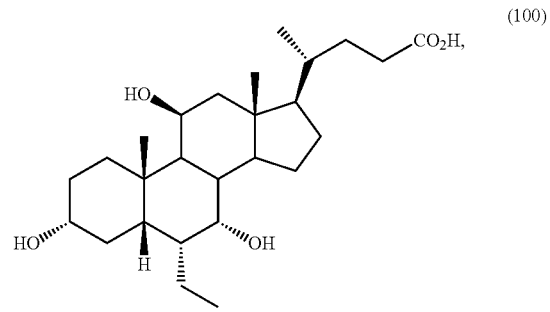 [SMILES: CC[C@H]1[C@@H](O)C2C3CC[C@H]([C@H](C)CCC(=O)O)[C@@]3(C)C[C@H](O)C2[C@@]2(C)CC[C@@H](O)C[C@@H]12]
(100)

or a pharmaceutically acceptable salt or amino acid conjugate thereof.

6. A method of treating nonalcoholic steatohepatitis (NASH) in a subject, comprising administering to the subject in need thereof an effective amount of compound 100

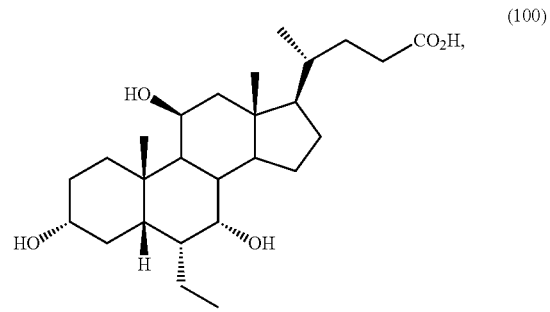 [SMILES: CC[C@H]1[C@@H](O)C2C3CC[C@H]([C@H](C)CCC(=O)O)[C@@]3(C)C[C@H](O)C2[C@@]2(C)CC[C@@H](O)C[C@@H]12]
(100)

or a pharmaceutically acceptable salt or amino acid conjugate thereof.

* * * * *